(12) United States Patent
Takahashi

(10) Patent No.: US 8,859,732 B2
(45) Date of Patent: Oct. 14, 2014

(54) BENZYLIC COMPOUND

(75) Inventor: Daisuke Takahashi, Mie (JP)

(73) Assignee: Ajinomoto Co., Inc., Tokyo (JP)

( * ) Notice: Subject to any disclaimer, the term of this patent is extended or adjusted under 35 U.S.C. 154(b) by 621 days.

(21) Appl. No.: 12/976,393

(22) Filed: Dec. 22, 2010

(65) Prior Publication Data
US 2011/0160433 A1 Jun. 30, 2011

Related U.S. Application Data

(60) Provisional application No. 61/290,371, filed on Dec. 28, 2009.

(30) Foreign Application Priority Data

Dec. 25, 2009 (JP) .................................. 2009-296366

(51) Int. Cl.
| | | |
|---|---|---|
| C07K 1/06 | (2006.01) | |
| C07C 43/23 | (2006.01) | |
| C07C 217/54 | (2006.01) | |
| C07C 235/40 | (2006.01) | |
| C07C 217/58 | (2006.01) | |

(52) U.S. Cl.
CPC ........... *C07C 217/58* (2013.01); *C07C 2101/14* (2013.01); *C07K 1/062* (2013.01); *C07C 235/40* (2013.01); *C07C 43/23* (2013.01)
USPC ............................ 530/335; 564/123; 568/608

(58) Field of Classification Search
USPC ............................ 530/335; 564/123; 568/608
See application file for complete search history.

(56) References Cited

U.S. PATENT DOCUMENTS

| | | | |
|---|---|---|---|
| 2,477,850 A | | 8/1949 | Alles et al. |
| 4,668,705 A | * | 5/1987 | Moeller et al. ................. 514/718 |
| 5,208,247 A | | 5/1993 | Trova et al. |
| 5,712,367 A | | 1/1998 | Bernard et al. |
| 2009/0299103 A1 | | 12/2009 | Chiba et al. |
| 2010/0029904 A1 | | 2/2010 | Chiba et al. |

FOREIGN PATENT DOCUMENTS

| | | |
|---|---|---|
| EP | 2 415 744 | 2/2012 |
| GB | 969921 | 9/1964 |
| JP | 60-61515 | 4/1985 |
| JP | 5-213877 | 8/1993 |
| JP | 2579699 | 11/1996 |
| JP | 9-507846 | 8/1997 |
| JP | 2000-44493 | 2/2000 |
| WO | WO 95/17888 | 7/1995 |
| WO | WO 2006/104166 A1 | 10/2006 |
| WO | WO 2007/034812 A1 | 3/2007 |
| WO | WO 2007/122847 A1 | 11/2007 |

OTHER PUBLICATIONS

Renaudet et al., Organic Letters (2004), 6(3), pp. 397-400.*
Hitoshi Tamiaki, et al., "A Novel Protecting Group for Constructing Combinatorial Peptide Libraries", Bull. Chem. Soc. Jpn., vol. 74, 2001, pp. 733-738.
International Search Report issued Apr. 5, 2011, in Patent Application No. PCT/JP2010/073251.
Virgil Percec, et al., "Designing Libraries of First Generation AB$_3$ and AB$_2$ Self-Assembling Dendrons via the Primary Structure Generated from Combinations of (AB)$_y$—AB$_3$ and (AB)$_y$—AB$_2$ Building Blocks", Journal of the American Chemical Society, vol. 126, No. 19, Apr. 23, 2004, pp. 6078-6094.
Supplementary European Search Report, dated Nov. 4, 2013.
M. Mizuno, et al., "Fluorous Glycopeptide Synthesis without Protection of Sugar Hydroxy Groups", Chemistry Letters, vol. 34, No. 3, 2005, pp. 426-427.
K. Goto, et al., "Synthesis of Peptides and Oligosaccharides by Using a Recyclable Fluorous Tag", Tetrahedron Letters, vol. 46, No. 48, 2005, pp. 8293-8297.

* cited by examiner

*Primary Examiner* — Yong Chu
(74) *Attorney, Agent, or Firm* — Oblon, Spivak, McClelland, Maier & Neustadt, L.L.P.

(57) ABSTRACT

The present invention provides a protecting reagent that can be removed in a high yield even under acidic conditions and can afford a resulting product at a high purity in an organic synthesis reaction such as peptide synthesis and the like. The inventive protecting reagent is particular benzylic compound having only one hydroxyl group substituted by an organic group having an aliphatic hydrocarbon group having a carbon number of not less than 14.

13 Claims, No Drawings

BENZYLIC COMPOUND

CROSS REFERENCES TO RELATED APPLICATIONS

This application claims priority to U.S. provisional application No. 61/290,371, filed on Dec. 28, 2009, and Japanese patent application No. 2009-296366, filed on Dec. 25, 2009, both of which are incorporated by this reference in their entireties.

FIELD OF THE INVENTION

The present invention relates to a particular benzylic compound usable as a protecting reagent of a carboxyl group or a C-terminal of an amino acid or a peptide, and the like in organic synthesis, particularly peptide synthesis, and the like, and a method of synthesizing a peptide using the benzylic compound.

BACKGROUND OF THE INVENTION

As a method of peptide synthesis, besides a solid phase method and a liquid phase method, a production method using a protecting group (hereinafter to be also referred to as anchor), comprising performing a reaction in a homogeneous liquid phase, changing the solvent composition after the reaction, and isolating and purifying the reaction mixture only by filtration and washing has recently been proposed.

Patent document 1 and non-patent document 1 each disclose a method comprising using a 3,4,5-tris(n-octadecyloxy)benzyl alcohol type compound as a protecting reagent of a carboxyl group and the like. However, an alkylation suppressive effect on removal of the protecting group is not described at all.

Patent documents 2-4 each disclose protecting reagents such as a 3,5-di(docosyloxy)benzyl alcohol type compound, a 2,4-di(docosyloxy)benzyl alcohol type compound and the like. However, an alkylation suppressive effect on removal of the protecting group is not described at all.

Patent document 4 also discloses a protecting reagent of a trityl type. However, the protecting group is not entirely satisfactory as an anchor since a side reaction such as dissociation thereof even in methanol and the like occur.

DOCUMENT LIST

Patent Documents patent document 1: JP-A-2000-44493
patent document 2: WO2006/104166
patent document 3: WO2007/034812
patent document 4: WO2007/122847

Non-Patent Document non-patent document 1: Bull. Chem. Soc. Jpn., 74, 733-738 (2001)

SUMMARY OF THE INVENTION

An object of the present invention is to provide a useful benzylic compound which enables an organic synthesis reaction to be performed in a homogeneous liquid phase, can be used as a protecting reagent (anchor) permitting isolation and purification by filtration and washing alone by changing the solvent composition after the reaction, and affords a resulting product in a high yield and at high purity while suppressing an alkylation reaction even under acidic conditions during deprotection.

The present inventors have found that a particular benzylic compound having only one hydroxyl group substituted by an organic group having an aliphatic hydrocarbon group having a carbon number of not less than 14 can solve the above-mentioned problem, which resulted in the completion of the present invention. The present invention is as described below.

[1] The present invention provides a benzylic compound represented by the formula (I):

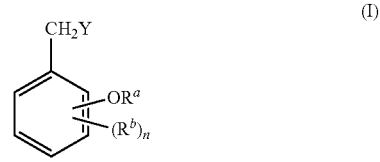

wherein

Y is a hydroxyl group or an —NHR group (R is a hydrogen atom, an alkyl group or an aralkyl group);

$R^a$ is an organic group having an aliphatic hydrocarbon group, which has a total carbon number of not less than 14;

$R^b$ in the number of n is each independently an alkoxy group having a carbon number of 1 to 6, a halogen atom, or an alkyl group having a carbon number of 1 to 6, which is optionally substituted by one or more halogen atoms; and n is an integer of 0-4.

[2] The benzylic compound of [1], wherein the total carbon number of the organic group for $R^a$ is 14-200.

[3] The benzylic compound of [1], wherein the total carbon number of the organic group for $R^a$ is 30-80.

[4] The benzylic compound of any of [1] to [3], wherein n is an integer of 0-2, and $R^b$ in the number of n is each independently an alkoxy group having a carbon number of 1 to 4.

[5] The benzylic compound of any of [1] to [4], wherein $R^a$ is a group represented by the formula (a):

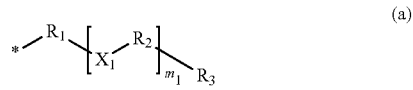

wherein

* indicates the position of a bond;

$m_1$ is an integer of 1-10;

$X_1$ in the number of $m_1$ is each independently a single bond, —O—, —S—, —COO—, —OCONH—, —NHCO— or —CONH—;

$R_1$ and $R_2$ in the number of $m_1$ are each independently a divalent aliphatic hydrocarbon group having a carbon number of not less than 5; and $R_3$ is a hydrogen atom, or a group represented by the formula (I'):

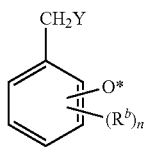
(I')

wherein * indicates the position of a bond; and other symbols are as defined in [1];

a group represented by the formula (b):

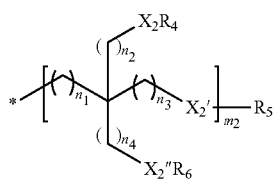
(b)

wherein
* indicates the position of a bond;
$m_2$ is 1 or 2;
$n_1$, $n_2$, $n_3$ and $n_4$ are each independently an integer of 0-2;
$X_2$ in the number of $m_2$, $X_2'$ in the number of $m_2$ and $X_2''$ in the number of $m_2$ are each independently a single bond, —O—, —S—, —COO—, —OCONH—, —NHCO— or —CONH—;
$R_4$ in the number of $m_2$ and $R_6$ in the number of $m_2$ are each independently a hydrogen atom, a methyl group or an aliphatic hydrocarbon group having a carbon number of not less than 5; and
$R_5$ is an aliphatic hydrocarbon group having a carbon number of not less than 5;

a group represented by the formula (c):

(c)

wherein
* indicates the position of a bond;
$m_3$ is an integer of 0-15;
$n_5$ is an integer of 0-11;
$n_6$ is an integer of 0-5;
$X_3$ in the number of $m_3$ is each independently a single bond, —O—, —S—, —COO—, —OCONH—, —NHCO— or —CONH—; and
$R_7$ in the number of $m_3$ is each independently a hydrogen atom, a methyl group or an aliphatic hydrocarbon group having a carbon number of not less than 5; or a group represented by the formula (d):

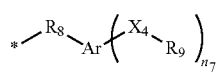
(d)

wherein
* indicates the position of a bond;
$X_4$ in the number of $n_7$ is a single bond, —O—, —S—, —COO—, —OCONH—, —NHCO— or —CONH;
$R_8$ is a divalent aliphatic hydrocarbon group;
$R_9$ in the number of $n_7$ is a monovalent aliphatic hydrocarbon group;
$n_7$ is an integer of 1-5; and
Ar is an arylene group.

[6] The benzylic compound of [5], wherein $R^a$ is a group represented by the formula (a) wherein $m_1$ is 1; $X_1$ is a single bond or —O—; $R_1$ and $R_2$ are each independently a divalent aliphatic hydrocarbon group having a carbon number of 5-80;
and $R_3$ is a hydrogen atom, or a group represented by the formula (I''):

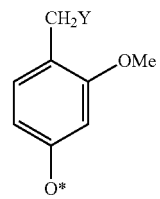
(I'')

wherein * indicates the position of a bond; and Y is as defined in [1], or the formula (I'''):

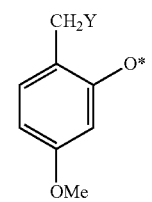
(I''')

wherein * indicates the position of a bond; and Y is as defined in [1];
a group represented by the formula (b) wherein $m_2$ is 1; $n_1$, $n_2$, $n_3$ and $n_4$ are each independently 0 or 1; $X_2$, $X_2'$ and $X_2''$ are each independently a single bond, or —O—; $R_4$ and $R_6$ are each independently a hydrogen atom, a methyl group or an aliphatic hydrocarbon group having a carbon number of 5 to 80; and $R_5$ is an aliphatic hydrocarbon group having a carbon number of 5 to 80;
a group represented by the formula (c) wherein $m_3$ is an integer of 1-5; $n_5$ is an integer of 0-2; $n_6$ is an integer of 0-3; $X_3$ in the number of $m_3$ is —O—; and $R_7$ in the number of $m_3$ is each independently an aliphatic hydrocarbon group having a carbon number of 5 to 80; or
a group represented by the formula (d) wherein $X_4$ in the number of $n_7$ is —O—; $R_8$ and $R_9$ in the number of $n_7$ are each independently a monovalent or divalent aliphatic hydrocarbon group having a carbon number of 5 to 80; $n_7$ is an integer of 1-3; and Ar is phenylene.

[7] The benzylic compound of [5], wherein $R^a$ is a group represented by the formula (a) wherein $m_1$ is 1; $X_1$ is —O—; $R_1$ and $R_2$ are each independently an alkylene group having a carbon number of 8 to 60; and $R_3$ is a hydrogen atom;
a group represented by the formula (b) wherein $m_2$ is 1; $n_1$, $n_2$, $n_3$ and $n_4$ are each 1; $X_2$, $X_2'$ and $X_2''$ are each —O—; and $R_4$, $R_5$ and $R_6$ are each independently an alkyl group having a carbon number of 8 to 60;

a group represented by the formula (c) wherein $m_3$ is 2 or 3; $n_5$ is 1; $n_6$ is 2 or 3; $X_3$ in the number of $m_3$ is —O—; and $R_7$ in the number of $m_3$ is each independently an alkyl group having a carbon number of 8 to 60; or a group represented by the formula (d) wherein $X_4$ in the number of $n_7$ is —O—; $R_8$ is an alkylene group having a carbon number of 1 to 3; $R_9$ in the number of $n_7$ is each independently an alkyl group having a carbon number of 8 to 60; $n_7$ is an integer of 1-3; and Ar is phenylene.

[8] The benzylic compound of [5], wherein $R^a$ is a group represented by the formula (a) wherein $m_1$ is 1; $X_1$ is —O—; $R_1$ and $R_2$ are each independently an alkylene group having a carbon number of 14 to 30; and $R_3$ is a hydrogen atom;

a group represented by the formula (b) wherein $m_2$ is 1; $n_1$, $n_2$, $n_3$ and $n_4$ are each 1; $X_2$, $X_2'$ and $X_2''$ are each —O—; and $R_4$, $R_5$ and $R_6$ are each independently an alkyl group having a carbon number of 14 to 30;

a group represented by the formula (c) wherein $m_3$ is 2 or 3; $n_5$ is 1; $n_6$ is 3; $X_3$ in the number of $m_3$ is —O—; and $R_7$ in the number of $m_3$ is each independently an alkyl group having a carbon number of 14 to 30; or a group represented by the formula (d) wherein $X_4$ in the number of $n_7$ is —O—; $R_8$ is an alkylene group having a carbon number of 1 to 3; $R_9$ in the number of $n_7$ is each independently an alkyl group having a carbon number of 14 to 30;

$n_7$ is 2 or 3; and

Ar is phenylene.

[9] The benzylic compound of any of [1] to [8], wherein the group $OR^a$ is present at the 2-position or the 4-position on the benzene ring.

[10] The benzylic compound of any of [1] to [9], wherein the group $R^b$ is a methoxy group.

[11] The benzylic compound of any of [1] to [10], wherein Y is a hydroxyl group.

[12] The benzylic compound of any of [1] to [10], wherein Y is an —NHR group wherein R is as defined in [1].

[13] The benzylic compound of [11] or [12], which is selected from the group consisting of 4-(12'-docosyloxy-1'-dodecyloxy)benzyl alcohol;

4-(12'-docosyloxy-1'-dodecyloxy)-2-methoxybenzyl alcohol;

4-(12'-docosyloxy-1'-dodecyloxy)-2-methoxybenzylamine;

2-(12'-docosyloxy-1'-dodecyloxy)-4-methoxybenzyl alcohol;

2-(12'-docosyloxy-1'-dodecyloxy)-4-methoxybenzylamine;

4-methoxy-2-[3',4',5'-tris(octadecyloxy)benzyloxy]benzyl alcohol;

2-[3',5'-di(docosyloxy)benzyloxy]-4-methoxybenzyl alcohol;

2-methoxy-4-[2',2',2'-tris(octadecyloxymethyl)ethoxy]benzyl alcohol;

2-methoxy-4-[2',2',2'-tris(octadecyloxymethyl)ethoxy]benzylamine;

4-methoxy-2-[3',4',5'-tris(octadecyloxy)cyclohexylmethyloxy]benzyl alcohol;

4-[3',4',5'-tris(octadecyloxy)cyclohexylmethyloxy]benzyl alcohol;

1,22-bis[12-(4-hydroxymethyl-3-methoxyphenoxy)dodecyloxy]docosane; and 1,22-bis[12-(2-hydroxymethyl-5-methoxyphenoxy)dodecyloxy]docosane.

[14] The benzylic compound of [11] or [12], which is selected from the group consisting of 2-docosyloxy-4-methoxybenzyl alcohol;

2-methoxy-4-[3',4',5'-tris(octadecyloxy)cyclohexylmethyloxy]benzyl alcohol;

3,5-dimethoxy-4-[3',4',5'-tris(octadecyloxy)cyclohexylmethyloxy]benzyl alcohol;

N-(4-hydroxymethyl-3-methoxyphenyl) 3,4,5-tris(octadecyloxy)cyclohexylcarboxamide;

N-(5-hydroxymethyl-2-methoxyphenyl) 3,4,5-tris(octadecyloxy)cyclohexylcarboxamide; and N-(4-hydroxymethylphenyl) 3,4,5-tris(octadecyloxy)cyclohexylcarboxamide.

[15] A reagent for protecting a carboxyl group of amino acid or peptide, comprising the benzylic compound of [11].

[16] A reagent for protecting the C-terminal of amino acid or peptide, comprising the benzylic compound of [11].

[17] A method of producing a peptide by a liquid phase synthesis process comprising the following steps;

(1) a step of bonding the benzylic compound of any of [1] to [14] to amino acid or peptide (bonding step), and (2) a step of precipitating a bonded product of the benzylic compound with amino acid or peptide obtained in the above-mentioned step (precipitation step).

[18] A method of producing a peptide by a liquid phase synthesis process comprising the following steps;

(1) a step of obtaining C-protected amino acid or C-protected peptide, comprising condensing the benzylic compound of any of [1] to [14] with the C-terminal of N-protected amino acid or N-protected peptide (C-terminal protection step), (2) a step of removing the protecting group of the N-terminal of the amino acid or peptide obtained in the above-mentioned step (deprotection step of N-terminal), (3) a step of condensing the N-terminal of the amino acid or peptide obtained in the above-mentioned step with N-protected amino acid or N-protected peptide (peptide chain elongation step), and (4) a step of precipitating the peptide obtained in the above-mentioned step (precipitation step).

[19] The method of [18], further comprising one or more repeats of the following steps (5)-(7);

(5) a step of deprotecting the N-terminal of the peptide obtained in the precipitation step (deprotection step of N-terminal), (6) a step of condensing the N-terminal of peptide obtained in the above-mentioned step with N-protected amino acid or N-protected peptide (peptide chain elongation step), and (7) a step of precipitating the peptide obtained in the above-mentioned step (precipitation step).

[20] The method of the above-mentioned [18] or [19], further comprising, after the precipitation step, a step of removing the protecting group (anchor) of the C-terminal of the peptide.

[21] A method of producing a peptide compound, comprising using the benzylic compound of any of the above-mentioned [1] to [14].

[22] A method of producing an organic compound, comprising using the benzylic compound of any of the above-mentioned [1] to [14].

[23] A benzylic compound adduct protected by the benzylic compound of any of the above-mentioned [1] to [14].

[24] A compound represented by the following formula (III):

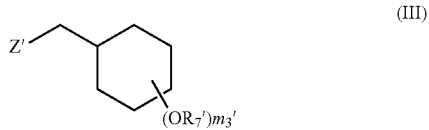

wherein $m_3'$ is 1-3; $R_7'$ in the number of $m_3'$ is an alkylene group having a carbon number of 14 to 30, and $Z'$ is a hydroxyl group or a leaving group.

[25] The compound of [24], wherein, in the formula (III), $m_3'$ is 3, and $Z'$ is a hydroxyl group, a halogen atom, an alkylsulfonyloxy group optionally substituted by one or more halogen atoms, or an optionally substituted arylsulfonyloxy group.

Using the particular benzylic compound of the present invention as a protecting reagent of a carboxyl group and the like, an organic synthesis reaction such as peptide synthesis and the like can be performed in a homogeneous liquid phase, and isolation and purification can be performed by filtration and washing alone by changing the solvent composition after the reaction. Furthermore, a resulting product can be obtained in a high yield and at high purity while suppressing an alkylation reaction even under acidic conditions during deprotection. Thus, the present invention also includes a method of producing a peptide compound, in which the improvement comprises protecting a functional group of the peptide with the benzylic compound according to any of the embodiments described above. The present invention also includes a method of producing an organic compound, where the improvement comprises protecting a functional group with the benzylic compound according to any of the embodiments described above.

DETAILED DESCRIPTION OF THE INVENTION

Unless otherwise specified in the sentences, any technical terms and scientific terms used in the present specification, have the same meaning as those generally understood by those of ordinary skill in the art in the art the present invention belongs to. Any methods and materials similar or equivalent to those described in the present specification can be used for practicing or testing the present invention, and preferable methods and materials are described in the following. All publications and patents referred to in the Specification are hereby incorporated by reference so as to describe and disclose constructed products and methodology described in, for example, publications usable in relation to the described invention.

The present invention relates to a particular benzylic compound (hereinafter to be abbreviated as the compound of the present invention).

The compound of the present invention is a protecting reagent to be introduced in organic synthesis reactions, preferably peptide synthesis and the like, as a protecting group (anchor) of a carboxyl group and the like, that is, C-terminal of amino acid or peptide, and the like, and the compound of the present invention suitable for the object can be appropriately selected.

The compound of the present invention is a benzylic compound represented by the following formula (I).

A benzylic compound represented by the formula (I):

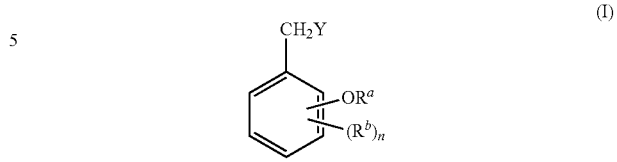

wherein
Y is a hydroxyl group or an —NHR group (R is a hydrogen atom, an alkyl group or an aralkyl group);
$R^a$ is an organic group having an aliphatic hydrocarbon group, which has a total carbon number of not less than 14;
$R^b$ in the number of n is each independently a $C_{1-6}$ alkoxy group, a halogen atom, or a $C_{1-6}$ alkyl group, which is optionally substituted by one or more halogen atoms;
when a plurality of $R^b$ are present, respective $R^b$ may be the same or different; and
n is an integer of 0-4.

The compound represented by the formula (I) of the present invention is bonded to a compound to be protected via group Y.

That is, the compound of the present invention wherein Y is a hydroxyl group or an —NHR group is bonded to the C-terminal etc. of amino acid or peptide for protection thereof.

In the present specification, examples of the "alkyl group" for R include a $C_{1-30}$ alkyl group, preferably a $C_{1-10}$ alkyl group, more preferably a $C_{1-6}$ alkyl group. Preferable examples include methyl, ethyl, propyl, isopropyl, butyl, isobutyl, sec-butyl, tert-butyl, and the like, and particularly preferred are methyl and ethyl.

In the present specification, examples of the "aralkyl group" for R include a $C_{7-30}$ aralkyl group. Preferred is a $C_{7-20}$ aralkyl group, more preferred is a $C_{7-16}$ aralkyl group (a $C_{6-40}$ aryl-$C_{1-6}$ alkyl group). Preferable examples include benzyl, 1-phenylethyl, 2-phenylethyl, 1-phenylpropyl, naphthylmethyl, 1-naphthylethyl, 1-naphthylpropyl, and the like, and particularly preferred is benzyl.

As R, a hydrogen atom, a $C_{1-6}$ alkyl group or a $C_{7-16}$ aralkyl group is preferable, a hydrogen atom, methyl, ethyl or benzyl is more preferable, and a hydrogen atom is particularly preferable.

In the present specification, the "organic group having an aliphatic hydrocarbon group" for $R^a$ means a monovalent organic group having an aliphatic hydrocarbon group in the molecular structure.

The "aliphatic hydrocarbon group" of the "organic group having an aliphatic hydrocarbon group" is an aliphatic hydrocarbon group consisting of straight chain or branched, saturated or unsaturated, and an aliphatic hydrocarbon group having a carbon number of not less than 5 is preferable, an aliphatic hydrocarbon group having a carbon number of 5 to 60 is particularly preferable, an aliphatic hydrocarbon group having a carbon number of 5 to 30 is more preferable, and an aliphatic hydrocarbon group having a carbon number of 10 to 30 is further preferable.

The site of the "aliphatic hydrocarbon group" in the organic group having an aliphatic hydrocarbon group of is not particularly limited, and it may be present at the terminal (monovalent group), or other site (e.g., divalent group).

Examples of the "aliphatic hydrocarbon group" include monovalent groups such as an alkyl group, a cycloalkyl group, an alkenyl group, a cycloalkenyl group, an alkynyl group and the like and divalent groups derived therefrom.

Preferred are monovalent groups such as a methyl group, an ethyl group, a propyl group, an isopropyl group, a butyl group, an isobutyl group, a sec-butyl group, a tert-butyl group, a pentyl group, a hexyl group, an octyl group, a decyl group, a dodecyl group, a lauryl group, a tridecyl group, a myristyl group, a cetyl group, a stearyl group, an aralkyl group, a behenyl group, an oleyl group, an isostearyl group and the like and divalent groups derived therefrom.

The moiety other than the "aliphatic hydrocarbon group" in the "organic group having an aliphatic hydrocarbon group" can be set freely. For example, —O—, —S—, —COO—, —OCONH— and —CONH—, and a moiety such as a hydrocarbon group (monovalent group or divalent group) and the like may be contained as a linker. Examples of the "hydrocarbon group" include an aliphatic hydrocarbon group, an aromatic aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As the "alkyl group", a $C_{1-6}$ alkyl group and the like are preferable and, for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group and the like are preferable and, for example, vinyl, 1-propenyl, allyl, isopropenyl, butenyl, isobutenyl and the like can be mentioned. As the "alkynyl group", a $C_{2-6}$ alkynyl group and the like are preferable and, for example, ethynyl, propargyl, 1-propynyl and the like can be mentioned. As the "cycloalkyl group", a $C_{3-6}$ cycloalkyl group and the like are preferable and, for example, cyclopropyl, cyclobutyl, cyclopentyl and cyclohexyl can be mentioned. As the "aryl group", for example, a $C_{6-14}$ aryl group and the like are preferable and, for example, phenyl, 1-naphthyl, 2-naphthyl, biphenylyl, 2-anthryl and the like can be mentioned. Of these, a $C_{6-10}$ aryl group is more preferable, and phenyl is particularly preferable. As the "aralkyl group", a $C_{7-20}$ aralkyl group is preferable and, for example, benzyl, 1-phenylethyl, 2-phenylethyl, 1-phenylpropyl, naphthylmethyl, 1-naphthylethyl, 1-naphthylpropyl and the like can be mentioned. Of these, a $C_{7-16}$ aralkyl group $C_{6-10}$ aryl-$O_{1-6}$ alkyl group) is more preferable, and benzyl is particularly preferable. The "hydrocarbon group" is optionally substituted by a substituent selected from a halogen atom (a chlorine atom, a bromine atom, a fluorine atom, an iodine atom), an alkyl group having a carbon number of 1 to 6, which is optionally substituted by one or more halogen atoms, an oxo group and the like.

The compound of the present invention has one $OR^a$ group. Here, the "organic group having an aliphatic hydrocarbon group" constituting the $OR^a$ group may have plural "aliphatic hydrocarbon groups" due to branching and the like. When the "organic group having an aliphatic hydrocarbon group" has plural "aliphatic hydrocarbon groups", they may be the same or different.

The $OR^a$ group is preferably bonded to, though unlimitatively, the 2-position or the 4-position on the benzene ring of the compound of the present invention, since the final removal of the anchor is facilitated.

In the compound of the present invention, the lower limit of the total carbon number of the "organic group having an aliphatic hydrocarbon group" for $R^a$ is preferably not less than 14, more preferably not less than 16, further preferably not less than 20, still more preferably not less than 24, and particularly preferably not less than 30. In the "organic group having an aliphatic hydrocarbon group" for $R^a$, the upper limit of the total carbon number is preferably not more than 200, more preferably not more than 150, further preferably not more than 120, still more preferably not more than 100, particularly preferably not more than 80, and not more than 60 is further particularly preferable. When the carbon number is higher, crystallinity of the compound of the present invention in a polar organic solvent becomes fine even when the peptide chain is a long chain.

Examples of the "organic group having an aliphatic hydrocarbon group" for $R^a$ include any group selected from the following formulas (a) to (d).

A group represented by the formula (a):

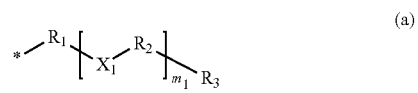

(a)

in the formula (a),

* indicates the position of a bond;

$m_1$ is an integer of 1-10;

$X_1$ in the number of $m_1$ is each independently a single bond, —O—, —S—, —COO—, —OCONH—, —NHCO— or —CONH—;

$R_1$ and $R_2$ in the number of $m_1$ are each independently a divalent aliphatic hydrocarbon group having a carbon number of not less than 5; and $R_3$ is a hydrogen atom, or the formula (I'):

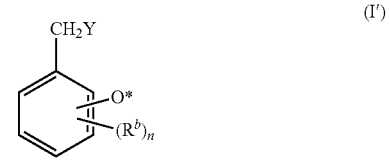

(I')

wherein * indicates the position of a bond, and other symbols are as defined above.

As the "aliphatic hydrocarbon group having a carbon number of not less than 5" for $R_1$ or $R_2$, the "aliphatic hydrocarbon group" of the above-mentioned "organic group having an aliphatic hydrocarbon group" having a carbon number of not less than 5 can be mentioned, preferably one having a carbon number of 5 to 80.

In the formula (a), a group wherein $m_1$ is 1;

$X_1$ is a single bond, or —O—;

$R_1$ and $R_2$ are each independently a divalent aliphatic hydrocarbon group having a carbon number of 5 to 80; and $R_3$ is a hydrogen atom, or the formula (I"):

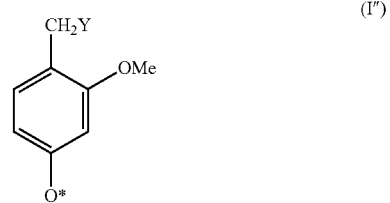

(I")

wherein * and Y are as defined above, or the formula (I'''):

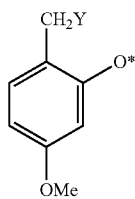

wherein * and Y are as defined above, is preferable. Of these, a group wherein
$m_1$ is 1;
$X_1$ is —O—;
$R_1$ and $R_2$ are each independently an alkylene group having a carbon number of 8 to 60; and
$R_3$ is a hydrogen atom, is more preferable.

Particularly preferable group of the formula (a) is a group wherein
$m_1$ is 1;
$X_1$ is —O—;
$R_1$ and $R_2$ are each independently an alkylene group having a carbon number of 14 to 30; and
$R_3$ is a hydrogen atom.

A group represented by the formula (b):

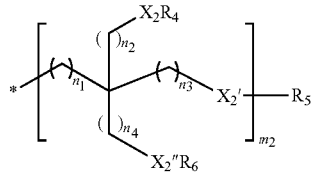

in the formula (b),
* indicates the position of a bond;
$m_2$ is 1 or 2;
$n_1$, $n_2$, $n_3$ and $n_4$ are each independently an integer of 0-2;
$X_2$ in the number of $m_2$, $X_2'$ in the number of $m_2$ and $X_2''$ in the number of $m_2$ are each independently a single bond, —O—, —S—, —COO—, —OCONH—, —NHCO— or —CONH—;
$R_4$ in the number of $m_2$ and $R_6$ in the number of $m_2$ are each independently a hydrogen atom, a methyl group or an aliphatic hydrocarbon group having a carbon number of not less than 5; and
$R_5$ is an aliphatic hydrocarbon group having a carbon number of not less than 5.

As the "aliphatic hydrocarbon group having a carbon number of not less than 5" for $R_4$, $R_5$ or $R_6$, the "aliphatic hydrocarbon group" having a carbon number of not less than 5, preferably 5 to 80, from the "aliphatic hydrocarbon group" of the above-mentioned "organic group having an aliphatic hydrocarbon group" can be mentioned.

In the formula (b), a group wherein
$m_2$ is 1;
$n_1$, $n_2$, $n_3$ and $n_4$ are each independently 0 or 1;
$X_2$, $X_2'$ and $X_2''$ are each independently a single bond or —O—;
$R_4$ and $R_6$ are each independently a hydrogen atom, a methyl group or an aliphatic hydrocarbon group having a carbon number of 5-80; and
$R_5$ is an aliphatic hydrocarbon group having a carbon number of 5-80 is preferable. Of these, a group wherein
$m_2$ is 1;
$n_1$, $n_2$, $n_3$ and $n_4$ are each 1;
$X_2$, $X_2'$ and $X_2''$ are each —O—;
$R_4$, $R_5$ and $R_6$ are each independently an alkyl group having a carbon number of 8 to 60 is more preferable.

Particularly preferable group of the formula (b) is a group wherein
$m_2$ is 1;
$n_1$, $n_2$, $n_3$ and $n_4$ are each 1;
$X_2$, $X_2'$ and $X_2''$ are each —O—; and
$R_4$, $R_5$ and $R_6$ are each independently an alkyl group having a carbon number of 14 to 30.

A group represented by the formula (c):

wherein
* indicates the position of a bond;
$m_3$ is an integer of 0-15;
$n_5$ is an integer of 0-11;
$n_6$ is an integer of 0-5;
$X_3$ in the number of $m_3$ is each independently a single bond, —O—, —S—, —COO—, —OCONH—, —NHCO— or —CONH—; and
$R_7$ in the number of $m_3$ is each independently a hydrogen atom, a methyl group or an aliphatic hydrocarbon group having a carbon number of not less than 5.

Examples of the "aliphatic hydrocarbon group having a carbon number of not less than 5" for $R_7$ include the "aliphatic hydrocarbon group" having a carbon number of not less than 5, preferably 5 to 80, from the "aliphatic hydrocarbon group" of the above-mentioned "organic group having an aliphatic hydrocarbon group".

In the formula (c), a group wherein
$m_3$ is an integer of 1-5;
$n_5$ is an integer of 0-2;
$n_6$ is an integer of 0-3;
$X_3$ in the number of $m_3$ is —O—; and
$R_7$ in the number of $m_3$ is each independently an aliphatic hydrocarbon group having a carbon number of 5-80 is preferable. Of these, a group wherein
$m_3$ is 2 or 3;
$n_5$ is 1;
$n_6$ is 2 or 3;
$X_3$ in the number of $m_3$ is —O—; and
$R_7$ in the number of $m_3$ is each independently an aliphatic hydrocarbon group having a carbon number of 8 to 60, is more preferable.

Particularly preferable group of the formula (c) is a group wherein
$m_3$ is 2 or 3;
$n_5$ is 1;
$n_6$ is 3;
$X_3$ in the number of $m_3$ is —O—; and
$R_7$ in the number of $m_3$ is each independently an alkyl group having a carbon number of 14 to 30.

A group represented by the formula (d):

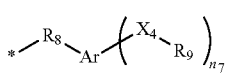

in the formula (d),
* indicates the position of a bond;
$X_4$ in the number of $n_7$ is a single bond, —O—, —S—, —COO—, —OCONH—, —NHCO— or —CONH—;
$R_8$ is a divalent aliphatic hydrocarbon group;
$R_9$ in the number of $n_7$ is a monovalent aliphatic hydrocarbon group;
$n_7$ is an integer of 1-5; and
Ar is an arylene group.

Examples of the "aliphatic hydrocarbon group" for $R_8$ or $R_9$ include those similar to the "aliphatic hydrocarbon group" of the above-mentioned "organic group having an aliphatic hydrocarbon group". Preferred are those having a carbon number of not less than 5, more preferably 5 to 80, particularly preferably 8 to 60.

Examples of the "arylene group" for Ar include phenylene, naphthylene, biphenylene and the like, preferably phenylene.

In the formula (d), a group wherein
$X_4$ in the number of $n_7$ is —O—;
$R_8$ and $R_9$ in the number of $n_7$ are each independently a monovalent or divalent aliphatic hydrocarbon group having a carbon number of 8 to 60;
$n_7$ is an integer of 1-3; and
Ar is phenylene is preferable. Of these, a group wherein
$X_4$ in the number of $n_7$ is —O—;
$R_8$ is an alkylene group having a carbon number of 1 to 3;
$R_9$ in the number of $n_7$ is each independently an alkyl group having a carbon number of 14 to 30,
$n_7$ is 2 or 3; and
Particularly preferable group of the formula (d) is a group wherein
$X_4$ in the number of $n_7$ is —O—;
$R_8$ is a methylene group;
$R_9$ in the number of $n_7$ is each independently an alkyl group having a carbon number of 14 to 30,
$n_7$ is 2 or 3; and
Ar is phenylene.

Specific examples of the "organic group having an aliphatic hydrocarbon group" include the following groups having an aliphatic carbon chain, which has a carbon number of 18 to 100. * in each group indicates the position of a bond.

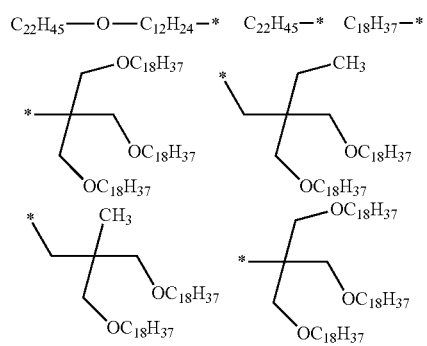

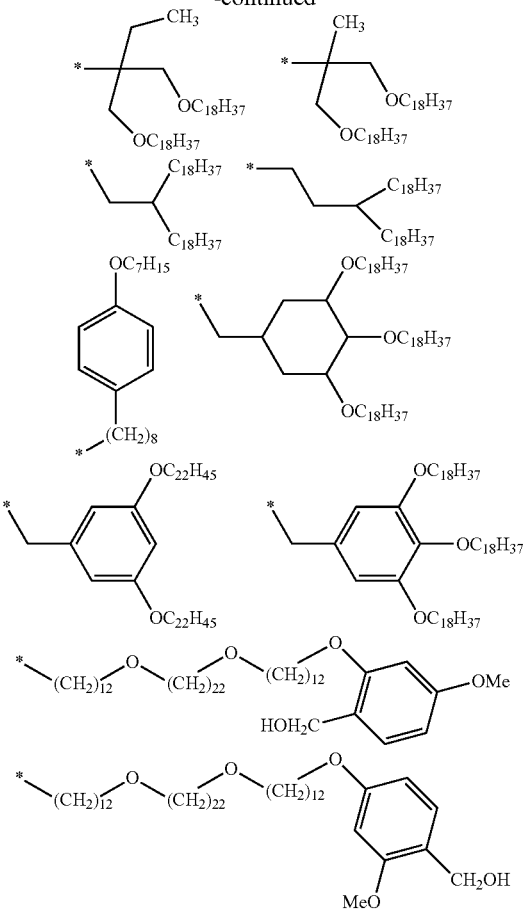

In the present specification, specific preferable examples of the "$R^b$ group" include a $C_{1-6}$ alkoxy group (e.g., a $C_{1-4}$ alkoxy group such as methoxy, ethoxy, propoxy, isopropoxy, butoxy, isobutoxy, sec-butoxy, tert-butoxy etc.), a $C_{1-6}$ alkyl group optionally substituted by one or more halogens (e.g., a $C_{1-6}$ alkyl group such as methyl, ethyl, propyl, isopropyl, butyl, isobutyl, sec-butyl, tert-butyl, pentyl, hexyl etc., a $C_{1-6}$ alkyl group substituted by halogen such as trifluoromethyl, trichloromethyl etc.), or a halogen atom. Of these, a $C_{1-6}$ alkoxy group (particularly a methoxy group) is preferable. The benzylic compound of the present invention preferably does not have the "$R^b$ group" on the benzene ring, or has a $C_{1-6}$ alkoxy group. The "$R^b$ group" is present in the number of n in total wherein n is an integer of 0 to 4, preferably 0 to 2, more preferably 0 or 1.

Preferable examples of the benzylic compound of the present invention include the following benzylic compounds.
4-(12'-docosyloxy-1'-dodecyloxy)benzyl alcohol;
4-(12'-docosyloxy-1'-dodecyloxy)-2-methoxybenzyl alcohol;
4-(12'-docosyloxy-1'-dodecyloxy)-2-methoxybenzylamine;
2-(12'-docosyloxy-1'-dodecyloxy)-4-methoxybenzyl alcohol;
2-(12'-docosyloxy-1'-dodecyloxy)-4-methoxybenzylamine;
2-docosyloxy-4-methoxybenzyl alcohol;
4-methoxy-2-[3',4',5'-tris(octadecyloxy)benzyloxy)benzyl alcohol;
2-[3',5'-di(docosyloxy)benzyloxy]-4-methoxybenzyl alcohol;

2-methoxy-4-(2',2',2'-tris(octadecyloxymethyl)ethoxy)benzyl alcohol;
2-methoxy-4-[2',2',2'-tris(octadecyloxymethyl)ethoxy]benzylamine;
4-methoxy-2-[3',4',5'-tris(octadecyloxy)cyclohexylmethyloxy]benzyl alcohol;
2-methoxy-4-[3',4',5'-tris(octadecyloxy)cyclohexylmethyloxy]benzyl alcohol;
4-[3',4',5'-tris(octadecyloxy)cyclohexylmethyloxy]benzyl alcohol;
3,5-dimethoxy-4-[3',4',5'-tris(octadecyloxy)cyclohexylmethyloxy]benzyl alcohol;
N-(4-hydroxymethyl-3-methoxyphenyl) 3,4,5-tris(octadecyloxy)cyclohexylcarboxamide;
N-(5-hydroxymethyl-2-methoxyphenyl) 3,4,5-tris(octadecyloxy)cyclohexylcarboxamide;
N-(4-hydroxymethylphenyl) 3,4,5-tris(octadecyloxy)cyclohexylcarboxamide;
1,22-bis[12-(4-hydroxymethyl-3-methoxyphenoxy)dodecyloxy]docosane; and
1,22-bis[12-(2-hydroxymethyl-5-methoxyphenoxy)dodecyloxy]docosane.

Production Method of the Compound of the Present Invention

While the production method of the compound of the present invention is not particularly limited, it can be synthesized, for example, via the following reactions.

Unless otherwise specified, the starting compound may be a commercially available product, or can be produced according to a method known per se or a method analogous thereto.

While the yield of the compound obtained by each of the following methods may vary depending on the reaction conditions employed, the compound can be isolated and purified from the resulting product by a general method (recrystallization, column chromatography and the like), and then precipitated by a method of changing the solution temperature, a method of changing the solution composition and the like.

In each reaction, when the starting compound has a hydroxy group, an amino group, a carboxy group, a carbonyl group or the like, a protecting group generally used in the peptide chemistry and the like may be introduced into these groups, and the object compound can be obtained by removing the protecting group as necessary after the reaction.

The compound of the present invention can be produced, for example, according to the following steps.

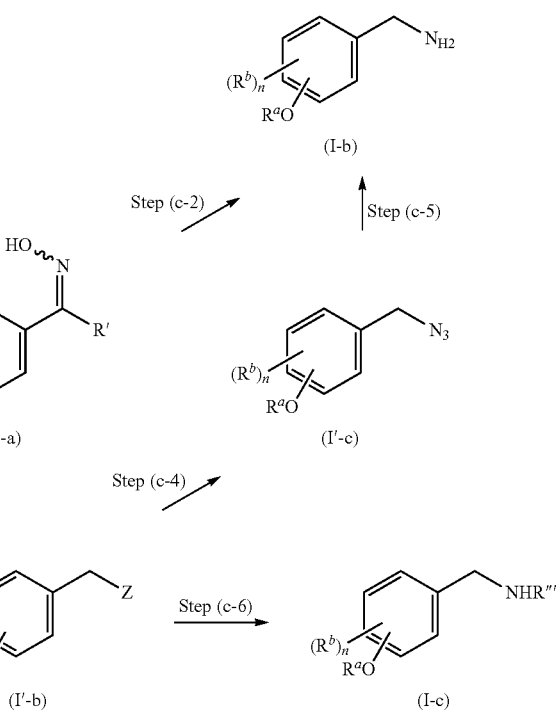

wherein R' is a hydrogen atom or OR" group (wherein R" is an alkyl group such as a $C_{1-6}$ alkyl group and the like, an aralkyl group such as a benzyl group etc., and the like), R''' is an alkyl group or an aralkyl group, Z is a leaving group such as a halogen atom and the like, and other symbols are as defined above.

Step (a)

In this step, group $R^a$ is introduced into a hydroxyl group of a compound represented by the formula (II) (hereinafter to be abbreviated as compound (II)) to give a compound represented by the formula (IIa) (hereinafter to be abbreviated as compound (IIa)).

The reaction is performed in a solvent that does not influence the reaction in the presence of a base by using halide corresponding to group $R^a$ (chloride, bromide or iodide), or an alkylsulfonyloxylated compound corresponding to group $R^a$ (e.g., a methanesulfonyloxylated compound etc.) or an arylsulfonyloxylated compound (e.g., a p-toluenesulfonyloxylated compound etc.), or under Mitsunobu reaction conditions of reacting compound (II) with alcohol corresponding to group $R^a$ in the presence of triphenylphosphine and diisopropyl azodicarboxylate.

Examples of the base include alkali metal salt such as sodium carbonate, sodium hydrogen carbonate, potassium carbonate, sodium hydride, potassium hydride, potassium tert-butoxide and the like; organic bases such as pyridine, triethylamine, N,N-dimethylaniline, 1,8-diazabicyclo[5.4.0]undec-7-ene etc., and the like. Of these, sodium carbonate, potassium carbonate, sodium hydride and the like are preferable.

Examples of the solvent include aromatic hydrocarbons such as toluene, xylene and the like; ethers such as tetrahydrofuran, dioxane and the like; amides such as dimethylformamide, dimethylacetamide and the like; halogenated hydrocarbons such as chloroform, dichloromethane and the like; nitriles such as acetonitrile and the like, and a mixture thereof. Of these, dimethylformamide, tetrahydrofuran, toluene, N-methylpyrrolidone and the like are preferable.

The reaction temperature is generally 50° C. to 150° C., preferably 60° C. to 130° C. The reaction time is generally 2-30 hr, preferably 3-10 hr.

Step (b)

In this step, compound (IIa) is reduced to give a compound represented by the formula (I-a) (hereinafter to be abbreviated as compound (I-a)). The reduction reaction can be performed by a method using a reducing agent.

Examples of the reducing agent to be used for the reduction reaction include metal hydride (sodium borohydride, lithium borohydride, sodium cyanoborohydride, sodium triacetoxyborohydride, dibutylaluminum hydride, aluminum hydride, lithium aluminum hydride, etc.) and the like. Of these, sodium borohydride, dibutylaluminum hydride and the like are preferable.

The reaction is performed in a solvent that does not influence the reaction. Examples of the solvent include alcohols such as methanol, ethanol and the like; ethers such as diethyl ether, tetrahydrofuran, dioxane and the like; aromatic hydrocarbons such as toluene, xylene and the like; and a mixture thereof. Of these, tetrahydrofuran, toluene and the like are preferable.

The reaction temperature is generally 0° C. to 100° C., preferably 30° C. to 70° C., and the reaction time is generally 1-24 hr, preferably 2-5 hr.

Step (c-1)

In this step, compound (IIa) (formula (IIa) wherein R' is a hydrogen atom) is oximated to give a compound represented by the formula (I'-a) (hereinafter to be abbreviated as compound (I'-a)).

The oximation reaction includes reacting compound (IIa) with hydroxylamine acid addition salt in a solvent that does not influence the reaction in the presence of a base.

Examples of the hydroxylamine acid addition salt include mineral acid salts such as hydrochloride, sulfate, nitrate and the like, organic acid salts such as acetate, trifluoroacetate, methanesulfonate, trifluoromethanesulfonate, p-toluenesulfonate etc., and the like, and hydrochloride is particularly preferable.

Examples of such base include alkali metal salts such as potassium hydroxide, sodium hydroxide, sodium hydrogen carbonate, potassium carbonate and the like; organic bases such as pyridine, triethylamine, diisopropylethylamine, N,N-dimethylaniline, 1,8-diazabicyclo[5.4.0]undec-7-ene etc., and the like. Of these, triethylamine, diisopropylethylamine and the like are preferably.

Examples of the solvent include halogen solvents such as chloroform, dichloromethane and the like; aromatic hydrocarbons such as toluene, xylene and the like; ethers such as tetrahydrofuran, dioxane and the like; and/or a mixture thereof. Of these, dichloromethane, chloroform, toluene and the like are preferable.

The reaction temperature is generally 10° C. to 100° C., preferably 20° C. to 60° C., and the reaction time is generally 0.5-30 hr, preferably 2-20 hr.

Step (c-2)

In this step, compound (I'-a) is reduced by a catalytic hydrogenation reaction in the presence of a metal catalyst such as palladium-carbon, Raney-nickel and the like, or by a reducing agent such as metal hydride and the like, which is similar to those in the aforementioned step (b), to give a compound represented by the formula (I-b) (hereinafter to be abbreviated as compound (I-b)), which is the compound of the present invention.

Compound (I-b) can also be produced from step (c-3) via step (c-4) and step (c-5).

Step (c-3)

In this step, compound (I-a) is halogenated with, for example, a chlorinating agent such as acetyl chloride, thionyl chloride and the like or, for example, a brominating agent such as acetyl bromide, phosphorus tribromide, diphenylphosphine/bromine and the like to give a compound represented by the formula (I'-b) (hereinafter to be abbreviated as compound (I'-b)).

Examples of the solvent include halogenated hydrocarbons such as chloroform, dichloromethane, and the like; aromatic hydrocarbons such as toluene, xylene, and the like; ethers such as tetrahydrofuran, dioxane, and the like; and a mixture thereof. Of these, chloroform, tetrahydrofuran, toluene, and the like are preferable.

The reaction temperature is generally 10° C. to 150° C., preferably 30° C. to 80° C., and the reaction time is generally 0.5-30 hr, preferably 2-20 hr.

Step (c-4)

In this step, compound (I'-b) is azidated with an azidating agent such as sodium azide and the like to give a compound represented by the formula (I'-c) (hereinafter to be abbreviated as compound (I'-c)).

The reaction includes reacting compound (I'-b) with an azidating agent in a solvent that does not influence the reaction.

Examples of the solvent include halogenated hydrocarbons such as chloroform, dichloromethane, and the like; aromatic hydrocarbons such as toluene, xylene, and the like; ethers such as tetrahydrofuran, dioxane, and the like; amides such as N,N-dimethylformamide and the like; and a mixture thereof. Of these, chloroform, N,N-dimethylformamide, and the like are preferable.

The reaction temperature is generally 10° C. to 150° C., preferably 20° C. to 100° C., and the reaction time is generally 0.5-30 hr, preferably 2-20 hr.

Step (c-5)

In this step, compound (I'-c) is aminated to give compound (I-b).

The reaction includes reacting compound (I'-c) with triphenylphosphine or catalytic hydrogenation in a solvent that does not influence the reaction in the presence of water.

The amount of triphenylphosphine to be used is preferably 1-10 mol, particularly preferably 1-5 mol, per 1 mol of compound (I'-c).

The amount of water to be used is preferably 1-10 mol, particularly preferably 1-5 mol, per 1 mol of compound (I'-c).

Examples of the solvent include aromatic hydrocarbons such as toluene, xylene, and the like; ethers such as tetrahydrofuran, dioxane, and the like; and a mixture thereof. Of these, toluene, tetrahydrofuran, and the like are preferable.

The reaction temperature is generally 10° C. to 150° C., preferably 20° C. to 100° C., and the reaction time is generally 0.5-30 hr, preferably 2-20 hr.

Step (c-6)

In this step, compound (I'-b) is reacted with R'''NH$_2$ (wherein R''' is as defined above) to give a compound represented by the formula (I-c) (hereinafter to be abbreviated as compound (I-c)), which is the compound of the present invention wherein Y is an —NHR''' group.

The reaction includes reacting compound (I'-b) with amine represented by R'''—NH$_2$ in a solvent that does not influence the reaction in the presence of, where necessary, for example, a base such as tertiary amine (triethylamine, diisopropylethylamine etc.) and the like.

Examples of the solvent include aromatic hydrocarbons such as toluene, xylene, and the like; ethers such as tetrahydrofuran, dioxane, and the like; and, halogenated hydrocarbons such as chloroform, dichloromethane, and the like and a mixture thereof. Of these, toluene, tetrahydrofuran, chloroform, and the like are preferable.

The reaction temperature is generally 10° C. to 100° C., preferably 20° C. to 60° C., and the reaction time is generally 0.5-30 hr, preferably 2-20 hr.

The halide corresponding to group R$^a$, which was used as a starting compound, may be a commercially available product, or can be produced by, for example, the following steps (d-1), (d-2), (e), (f), (g), or a method similar thereto.

Step (d-1)

$$H-R_2-OH + Hal-R_1-Hal \longrightarrow$$
(1) (2)

$$H-R_2-O-R_1-Hal$$
(3)

wherein Hal is a halogen atom (a chlorine atom, a bromine atom, an iodine atom, a fluorine atom; preferably a bromine atom or an iodine atom), and R$_1$ and R$_2$ are as defined above.

In this step, compound (3) is obtained by reacting 1-5 mol of compound (2) with 1 mol of compound (1). This step is performed in the presence of a base in a solvent that does not adversely influence the reaction.

Examples of such base include alkali metal salts such as potassium hydroxide, sodium hydroxide, sodium hydrogen carbonate, potassium carbonate and the like; organic bases such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide etc., and the like.

Examples of such solvent include halogenated hydrocarbons such as chloroform, dichloromethane and the like; and nonpolar organic solvents such as 1,4-dioxane, tetrahydrofuran and the like. These solvents may be used in a mixture of two or more kinds thereof at an appropriate ratio. Preferred is tetrahydrofuran.

The reaction temperature is generally 20° C. to 150° C., preferably 50° C. to 100° C. The reaction time is generally 1-30 hr.

Step (d-2)

wherein each symbol is as defined above.

In this step, 0.3-5 mol of compound (4) is reacted with 1 mol of compound (5) to give compound (6). This step is performed in the presence of a base similar to those used in step (d-1) in a solvent that does not adversely influence the reaction. Compound (I) wherein R$^a$ is a group represented by the formula (a) wherein R$_3$ is the formula (I') can be synthesized by reacting 0.5-5 mol of compound (6) with 1 mol of compound (II), followed by a reduction step.

Step (e)

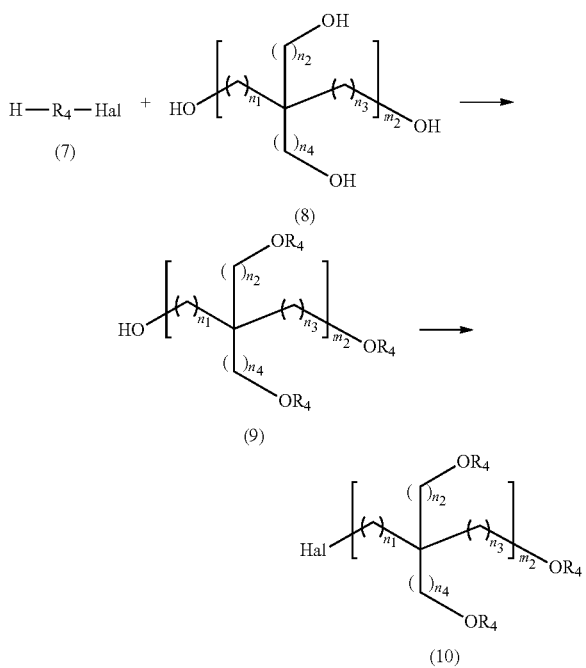

wherein each group is as defined above.

In this step, 0.2-5 mol of compound (8) is reacted with 1 mol of compound (7) to give compound (9), and the hydroxyl group of compound (9) is substituted by halogen to give compound (10). The reaction of compound (7) with compound (8) is performed in the presence of a base in a solvent that does not adversely influence the reaction.

Examples of such base include alkali metal salts such as potassium hydroxide, sodium hydroxide, sodium hydrogen carbonate, potassium carbonate and the like; organic bases such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide etc., and the like.

Examples of such solvent include aromatic hydrocarbons such as benzene, toluene, xylene and the like; nitriles such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc., and the like. These solvents may be used in a mixture of two or more kinds thereof at an appropriate ratio. Preferred is dimethylformamide. The amount of the solvent to be used is preferable 2- to 50-fold volume relative to compound (7).

The reaction temperature is generally 20° C. to 150° C., preferably 50° C. to 100° C. The reaction time is generally 1-30 hr.

The step of substituting the hydroxyl group of compound (9) to halogen to give compound (10) can be performed by reacting compound (9) with triphenylphosphine and halogen source in a solvent that does not adversely influence the reaction. This step is preferably performed in the presence of imidazole. Examples of the halogen source include carbon tetrachloride, hexachloroacetone, triphosgene (chlorine source), carbon tetrabromide (bromine source), iodomethane, iodine (iodine source) and the like. The amount of triphenylphosphine to be used is preferably 0.1-5 mol per 1 mol of compound (9), and the amount of the halogen source to be used is preferably 1-5 mol per 1 mol of compound (9). When imidazole is used, the amount thereof to be used is preferably 0.1-5 mol per 1 mol of compound (9).

Examples of such solvent include aromatic hydrocarbons such as benzene, toluene, xylene and the like; nitriles such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc. and the like. These solvents may be used in a mixture of two or more kinds thereof at an appropriate ratio. Preferred is toluene. The amount of the solvent to be used is preferably 3- to 50-fold volume relative to compound (9).

The reaction temperature is generally 30° C. to 150° C., preferably 40° C. to 120° C. The reaction time is generally 0.5-24 hr.

Step (f)

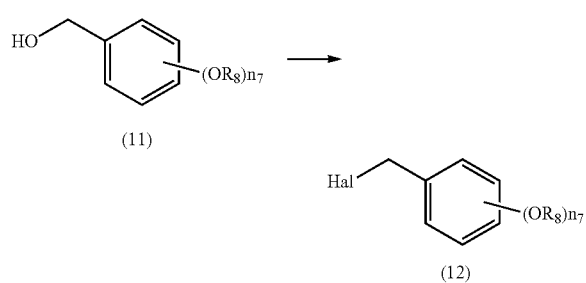

In this step, 1-5 mol of a halogenating agent (a chlorinating agent such as acetyl chloride, thionyl chloride and the like, a brominating agent such as acetyl bromide, phosphorus tribromide, diphenylphosphine/bromine etc., and the like) is reacted with 1 mol of compound (11) to give compound (12). This reaction is performed in a solvent that does not adversely influence the reaction.

Examples of such solvent include halogenated hydrocarbons such as chloroform, dichloromethane and the like; aromatic hydrocarbons such as benzene, toluene, xylene and the like; ethers such as 1,4-dioxane, diethyl ether and the like; and the like. These solvents may be used in a mixture of two or more kinds thereof at an appropriate ratio. Preferred are chloroform and N,N-dimethylformamide. The amount of the solvent to be used is preferably 2- to 50-fold volume relative to compound (11).

The reaction temperature is generally 0° C. to 100° C., preferably 0° C. to 30° C. The reaction time is generally 0.5-30 hr.

Step (g)

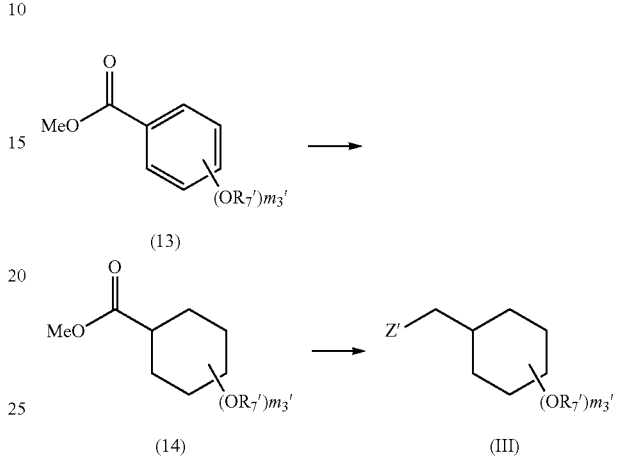

wherein Z' is a hydroxyl group or a leaving group, $m_3'$ is 1-3, preferably 3, and $R_7'$ is as defined above.

In this step, compound (13) is subjected to catalytic hydrogenation reaction with a catalyst such as rhodium-carbon (Rh/C) and the like to give compound (14), and the ester moiety of compound (14) is further reduced to give compound (III) wherein Z' is a hydroxyl group. This step also encompasses a step of obtaining compound (III) wherein Z' is a leaving group by conversion of a hydroxyl group to a halogen group, an alkylsulfonyloxy group optionally substituted by one or more halogen atoms (e.g., methanesulfonyloxy group etc.), an optionally substituted arylsulfonyloxy group (e.g., p-toluenesulfonyloxy group etc.) and the like. This reaction is performed in a solvent that does not adversely influence the reaction.

The "alkyl" or "aryl" in the "alkylsulfonyloxy group optionally substituted by one or more halogen atoms" and "arylsulfonyloxy group" is a group defined above, and the "substituent" of the "optionally substituted arylsulfonyloxy group" is a halogen atom, an alkyl group having a carbon number of 1 to 6, which is optionally substituted by one or more halogen atoms, an alkoxy group having a carbon number of 1 to 6 and the like.

Examples of the reducing agent to be used for the reduction reaction include metal hydride (sodium borohydride, lithium borohydride, sodium cyanoborohydride, sodium triacetoxyborohydride, dibutylaluminum hydride, aluminum hydride, lithium aluminum hydride etc.) and the like. Of these, dibutylaluminum hydride and the like are preferable.

The reaction is performed in a solvent that does not influence the reaction. Examples of the solvent include alcohols such as methanol, ethanol and the like; ethers such as diethyl ether, tetrahydrofuran, dioxane and the like; aromatic hydrocarbons such as toluene, xylene and the like; and a mixture thereof. Of these, tetrahydrofuran, toluene and the like are preferable.

The reaction temperature is generally −10° C. to 100° C., preferably 0° C. to 70° C., and the reaction time is generally 1-24 hr, preferably 2-5 hr.

Examples of the reagent to be used for the conversion to the leaving group include, besides the chlorinating agents and the brominating agents exemplified in the above-mentioned step (f), alkylsulfonylating agents such as methanesulfonyl chloride, trifluoromethanesulfonyl chloride and the like, arylsulfonylating agents such as benzenesulfonyl chloride, p-toluenesulfonyl chloride etc., and the like. Of these, an arylsulfonylating agent is preferable.

The reaction is performed in a solvent that does not influence the reaction. Examples of the solvent include halogenated hydrocarbons such as chloroform, dichloromethane and the like; aromatic hydrocarbons such as benzene, toluene, xylene and the like; nitriles such as acetonitrile, propionitrile and the like; ethers such as tetrahydrofuran, 1,4-dioxane, diethyl ether and the like. Of these, halogenated hydrocarbons such as chloroform and the like are preferable.

The reaction is preferably performed in the presence of 1-5 mol of an organic base such as pyridine and the like and 0.05-0.8 mol of an N,N-dimethyl-4-aminopyridine catalyst, per 1 mol of compound (15).

The reaction temperature is generally 0-100° C., preferably 0-70° C., and the reaction time is generally 1-24 hr, preferably 2-5 hr.

Using compounds (3), (6), (10), (12) and (16) obtained in steps (d-1), (d-2), (e), (f) and (g), the reaction of the above-mentioned step (a) can be performed to give compound (IIa), which is a useful intermediate for the production of the compound of the present invention. In the scheme, the carbon number of aliphatic hydrocarbon group, the kind of halogen atom, reaction reagents and the like are shown for the sake of convenience, and can be appropriately changed within the scope of the above-mentioned definitions.

[Organic Synthesis Reaction]

The compound of the present invention can be used as a reagent to protect a carboxyl group and the like, that is, a protecting reagent for amino acid or peptide, in organic synthesis reactions, preferably peptide synthesis and the like. Specifically, it is preferably introduced as a protecting group (anchor) of C-terminal functional groups such as a carboxyl group, a carboxamide group, a thiol group and the like, and side chain functional groups (hereinafter to be referred to as C-terminal etc.). When using as a protecting reagent, the compound may be activated to allow reaction with a substituent to be protected, or may be converted to an equivalent to allow reaction. The "organic compound protected by the benzylic compound of the present invention" is hereinafter sometimes referred to as a "benzylic compound adduct".

The benzylic compound of the present invention can be used as a protecting reagent (anchor) for various organic synthesis reactions. For example, the following steps can be performed.

step (i) a step of dissolving the compound of the present invention in soluble solvent (dissolution step), step (ii) a step of bonding the compound of the present invention dissolved in soluble solvent as obtained in the above-mentioned step to a reaction substrate (bonding step), step (iii) a step of precipitating the bonded product obtained in the above-mentioned step (precipitation step), and step (iv) a step of redissolving the bonded product obtained in the above-mentioned step or a product resulting from the reaction in a soluble solvent, and removing the anchor from the bonded product or the resulting product (deprotection step).

Step (i) (Dissolution Step)

In this step, the compound of the present invention is dissolved in a soluble solvent.

As the solvent, a general organic solvent can be used. Since superior reactivity can be expected when the solubility in the solvent is higher, a solvent in which the compound of the present invention shows high solubility is preferably selected. Specifically, halogenated hydrocarbon such as chloroform, dichloromethane and the like; and a nonpolar organic solvent such as 1,4-dioxane, tetrahydrofuran and the like can be mentioned. These solvents may be used in a mixture of two or more kinds thereof at an appropriate ratio. In addition, the above-mentioned halogenated hydrocarbons and nonpolar organic solvent may be mixed with aromatic hydrocarbons such as benzene, toluene, xylene and the like; nitriles such as acetonitrile, propionitrile and the like; ketones such as acetone, 2-butanone and the like; amides such as N,N-dimethylformamide and the like; sulfoxides such as dimethyl sulfoxide and the like at an appropriate ratio and used as long as the compound of the present invention is dissolved.

Step (ii) (Bonding Step)

In this step, the compound of the present invention dissolved in a soluble solvent, which is obtained in the above-mentioned step (i), is bonded to a reaction substrate.

Here, the reaction substrate has a —COOH group of protected amino acid and the like, and the amount of the reaction substrate to be used is 1-10 mol, preferably 1-5 mol, per 1 mol of the compound of the present invention.

When Y is a hydroxyl group, an ester bond can be formed by adding a condensing agent into a solvent that does not influence the reaction in the presence of a dimethylaminopyridine catalyst.

When Y is a group NHR, an amide bond can be formed by adding a condensing agent in the presence of a condensation additive (condensation promoter) such as 1-hydroxybenzotriazole (HOBt), ethyl 1-hydroxy-1H-1,2,3-triazole-5-carboxylate (HOCt), 1-hydroxy-7-azabenzotriazole (HOAt) and the like.

The amount of the condensation additive to be used is preferably 0.05-1.5 mol per 1 mol of the compound of the present invention.

Examples of the condensing agent include dicyclohexylcarbodiimide (DCC), diisopropylcarbodiimide (DIC), N-ethyl-N'-3-dimethylaminopropylcarbodiimide and hydrochloride thereof (EDC HCl), hexafluorophosphoric acid (benzotriazol-1-yloxy)tripyrrolizinophosphonium (PyBop), O-(benzotriazol-1-yl)-N,N,N',N'-tetramethyluronium tetrafluoroborate (TBTU), 1-[bis(dimethylamino)methylene]-5-chloro-1H-benzotriazolium 3-oxide hexafluorophosphate (HCTU), O-benzotriazole-N,N,N',N'-tetramethyluronium hexafluoroborate (HBTU), and the like.

The amount of the condensing agent to be used is 1-10 mol, preferably 1-5 mol, per 1 mol of the compound of the present invention.

Examples of the solvent include aromatic hydrocarbons such as toluene, xylene and the like; ethers such as diethyl ether, tetrahydrofuran, dioxane and the like; halogenated hydrocarbons such as chloroform, dichloromethane etc., and the like, and a mixture thereof. Of these, toluene, tetrahydrofuran and the like are preferable.

The reaction temperature is generally −10° C. to 30° C., preferably 0° C. to 20° C., and the reaction time is generally 1-30 hr.

For confirmation of the progress of the reaction, a method similar to general liquid phase organic synthesis reaction can be applied. That is, thin layer silica gel chromatography, high performance liquid chromatography and the like can be used to track the reaction.

Step (iii) (Precipitation Step)

In this step, the bonded product obtained in the above-mentioned step (ii), or a product obtained by dissolving the bonded product in a soluble solvent and performing a desired organic synthesis reaction is isolated by changing the solvent in which the bonded product or the resulting product is dissolved (e.g., change of solvent composition, change of solvent kind) to allow precipitation. That is, the reaction is performed under the conditions where the bonded product is dissolved and, after the reaction, the solvent is evaporated, and then substituted to allow precipitation of the bonded product and remove impurities. As the substitution solvent, polar organic solvents such as methanol, acetonitrile, and the like are used. That is, the reaction is performed under conditions where the compound can be dissolved and, for solvent substitution after the reaction, halogenated solvents, THF and the like are used for dissolution and polar organic solvents such as methanol, acetonitrile and the like are used for precipitation.

Step (iv) (Deprotection Step)

In this step, the protecting reagent (anchor) derived from the compound of the present invention is finally removed from the bonded product or resulting product isolated by precipitation in the above-mentioned step (iii) to give the object compound.

An anchor to be removed here is a group represented by the formula (I-d):

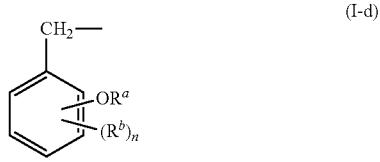

(I-d)

wherein each group is as defined above.

When Y is a hydroxyl group, it reacts with —COOH of the initial reaction substrate to form an ester bond. After deprotection, the C-terminal of peptide becomes —COOH. On the other hand, when Y is an —NHR group, the —COOH group of the reaction substrate becomes an amide bond and, by removal of the anchor, the C-terminal is converted to a —CONHR group.

When only an anchor wherein Y is a hydroxyl group needs to be selectively removed, an anchor wherein $OR^a$ is present at the 2-position or 4-position on the benzene ring is used as the compound of the present invention, and the deprotection is preferably performed by an acid treatment. Examples of the acid to be used include trifluoroacetic acid (hereinafter to be referred to as TFA), hydrochloric acid, sulfuric acid, methanesulfonic acid, p-toluenesulfonic acid and the like, with preference given to TFA. The deprotection is preferably performed under solution conditions using a solution such as chloroform, dichloromethane and THF, having an acid concentration of 0.1%-5%.

It is also possible to remove an anchor wherein Y is a hydroxyl group or —NHR group simultaneously with other peptide-protecting group. In this case, a method conventionally used in the pertinent field, particularly peptide synthesis, is used, with preference given to a method including addition of an acid and the like. As an acid, TFA, hydrochloric acid, sulfuric acid, mesylic acid, tosylic acid, trifluoroethanol, hexafluoroisopropanol and the like can be used. Of these, TFA is particularly preferable.

The amount of the acid to be used is appropriately determined according to the kind of the acid to be used, and an amount suitable for removing the anchor is used. The amount that can be used is 3-100 mol, preferably 5-50 mol, per 1 mol of the bonded product. When an acid is used, trifluoromethanesulfonic acid, trimethylsilyl trifluoromethanesulfonate, $BF_3Et_2O$ and the like can also be added as a further strong acid source.

The reaction temperature is generally 0° C. to 80° C., preferably 0° C. to 30° C. The reaction time is generally 0.5-24 hr.

By utilizing the above-mentioned steps, peptide can be produced. The benzylic compound of the present invention can be mainly used as, but is not limited to, a protecting reagent for C-terminal of amino acid or peptide and the like. In addition, since the benzylic compound of the present invention wherein Y is a hydroxyl group can be converted to a corresponding chloroformate form by a method conventionally used in the pertinent field, for example, reaction with phosgene, the chloroformate form can also be used as a protecting reagent of N-terminal and the like.

A method of producing a peptide utilizing the above-mentioned steps, comprising the following steps;

(1) a step of obtaining C-protected amino acid or C-protected peptide, comprising condensing the benzylic compound of the present invention with the C-terminal of N-protected amino acid or N-protected peptide (C-terminal protection step), (2) a step of removing a temporary protecting group of the N-terminal of the amino acid or peptide obtained in the above-mentioned step (deprotection step of N-terminal), (3) a step of condensing the N-terminal of the amino acid or peptide obtained in the above-mentioned step with N-protected amino acid or N-protected peptide (peptide chain elongation step), and (4) a step of precipitating the peptide obtained in the above-mentioned step (precipitation step).

Step (1) (C-Terminal Protection Step)

In this step, the benzylic compound of the present invention is condensed with the C-terminal of N-protected amino acid or N-protected peptide to give C-protected amino acid or C-protected peptide, i.e., benzylic compound adduct. For example, the step can be performed according to the above-mentioned binding step.

In the present invention, the "N-protected amino acid" and "N-protected peptide" mean amino acid and peptide wherein amino group is protected and carboxyl group is unprotected, and may be referred to as "P-AA-OH" (P is amino-protecting group (or temporary protecting group on demand)).

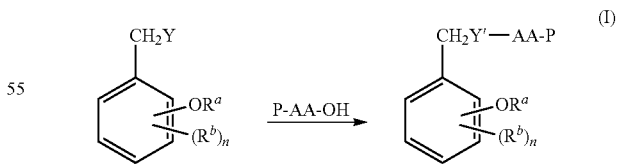

(I)

wherein P is an amino-protecting group, AA is a group derived from amino acid, Y' is O or NR and other symbols are as defined above.

The condensation reaction of the benzylic compound of the present invention and C-terminal of N-protected amino acid or N-protected peptide is preferably performed in a solvent that does not influence the reaction. For example, the reaction is performed in the presence of a condensing agent when Y is a hydroxyl group or —NHR group, and an ester bond is formed when Y is hydroxyl, and amide bond is formed when Y is an —NHR group. Examples of the condensing agent include dicyclohexylcarbodiimide, diisopropylcarbodiimide, N-ethyl-N'-3-dimethylaminopropylcarbodiimide and a hydrochloride thereof (EDC.HCl), and the like. An ester bond forming reaction is performed in the presence of dimethylaminopyridine, and an amide bond forming reaction is performed in the presence of a condensation additive such as HOBt, HOCt and the like.

Examples of the solvent to be used for the step include halogenated hydrocarbons such as chloroform, dichloromethane and the like; and nonpolar organic solvents such as 1,4-dioxane, tetrahydrofuran and the like. These solvents may be used in a mixture of two or more kinds thereof at an appropriate ratio, and preferred is chloroform. The amount of the solvent to be used is preferably 2- to 50-fold volume relative to the benzylic compound of the present invention.

The reaction temperature is generally −10° C. to 40° C., preferably 0° C. to 30° C. The reaction time is generally 1-70 hr.

Step (2) (N-Terminal Deprotection Step)

In this step, the temporary protecting group of the N-terminal of amino acid or peptide obtained in the above-mentioned step (1) is removed.

As the temporary protecting group of the N-terminal, the below-mentioned amino-protecting groups generally used in the technical field of peptide chemistry and the like are usable. In the present invention, a tert-butoxycarbonyl group (hereinafter to be also referred to as Boc group), a benzyloxycarbonyl group and/or a 9-fluorenylmethoxycarbonyl group (hereinafter to be also referred to as Fmoc group) are/is preferably used.

While the deprotection conditions are appropriately selected depending on the kind of the temporary protecting group, a group that can be removed under conditions different from removal of the protecting reagent derived from the compound of the present invention is preferable. For example, Fmoc group can be removed by a treatment with a base, and Boc group can be removed by a treatment with an acid. The reaction is performed in a solvent which does not influence the reaction.

Examples of the base include dimethylamine, diethylamine and the like. Examples of the solvent include halogenated hydrocarbons such as chloroform, dichloromethane, and the like; aromatic hydrocarbons such as toluene, xylene, and the like; ethers such as diethyl ether, tetrahydrofuran, dioxane, and the like; nitriles such as acetonitrile and the like, and a mixture thereof.

Step (3) (Peptide Chain Elongation Step)

In this step, the N-terminal of amino acid or peptide deprotected in N-terminal in step (2) is condensed with N-protected amino acid or N-protected peptide.

This step is performed by using the condensing agent, condensation additive and the like described in the aforementioned step (1) and under peptide synthesis conditions generally used in the field of peptide chemistry.

Step (4) (Precipitation Step)

This step is performed in the same manner as in the precipitation step in the above-mentioned step (iii).

In the production method of the peptide of the present invention, the N-protected amino acid or N-protected peptide obtained in step (4) can be subjected to steps (5)-(7) in a desired number of repeats:

(5) a step of removing the temporary protecting group of N-terminal of the peptide obtained in the precipitation step, (6) a step of condensing N-protected amino acid or N-protected peptide with N-terminal of the peptide obtained in the above-mentioned step, and (7) a step of precipitating the peptide obtained in the above-mentioned step.

Step (5)

The step is performed in the same manner as in the deprotection step of N-terminal in step (2).

Step (6)

This step is performed in the same manner as in the peptide chain elongation step of step (3).

Step (7)

This step is performed in the same manner as in the precipitation step of step (iii).

In the production method of the peptide of the present invention, a step of deprotecting the C-terminal of the peptide, wherein the C-terminal is protected with the benzylic compound, may be further contained after the precipitation step of step (4) or step (7). For example, the step can be performed according to the above-mentioned step (iv) for deprotection of the anchor of the present invention.

When the organic synthesis reaction or peptide synthesis reaction of the present invention contains multi-steps, the aforementioned precipitation step may be appropriately omitted as long as the reaction in the next step is not influenced.

In each reaction, when the starting compound has a hydroxy group, an amino group, a carboxy group or a carbonyl group (particularly when amino acid or peptide has a functional group in the side chain), a protecting group generally used in the peptide chemistry and the like may be introduced into these groups, and the object compound can be obtained by removing the protecting group as necessary after the reaction.

Examples of the hydroxyl-protecting group include ($C_1$-$C_6$)alkyl group (e.g., methyl, ethyl, propyl, isopropyl, butyl, tert-butyl), phenyl group, trityl group, ($C_7$-$C_{10}$)aralkyl group (e.g., benzyl), formyl group, ($C_1$-$C_6$)alkyl-carbonyl group (e.g., acetyl, propionyl), benzoyl group, ($C_7$-$C_{10}$)aralkyl-carbonyl group (e.g., benzylcarbonyl), 2-tetrahydropyranyl group, 2-tetrahydrofuranyl group, silyl group (e.g., trimethylsilyl, triethylsilyl, dimethylphenylsilyl, tert-butyldimethylsilyl, tert-butyldiethylsilyl), ($C_2$-$C_6$)alkenyl group (e.g., 1-allyl) and the like. These groups are optionally substituted by 1 to 3 substituents selected from a halogen atom (e.g., fluorine, chlorine, bromine, iodine), a ($C_1$-$C_6$)alkyl group (e.g., methyl, ethyl, propyl), a ($C_1$-$C_6$)alkoxy group (e.g., methoxy, ethoxy, propoxy), a nitro group and the like.

Examples of the amino-protecting group include formyl group, ($C_1$-$C_6$)alkyl-carbonyl group (e.g., acetyl, propionyl), ($C_1$-$C_6$)alkoxy-carbonyl group (e.g., methoxycarbonyl, ethoxycarbonyl, Boc group), benzoyl group, ($C_7$-$C_{10}$) aralkyl-carbonyl group (e.g., benzylcarbonyl), ($C_7$-$C_{19}$) aralkyloxy-carbonyl group (e.g., benzyloxycarbonyl, Fmoc group), trityl group, phthaloyl group, N,N-dimethylaminomethylene group, silyl group (e.g., trimethylsilyl, triethylsilyl, dimethylphenylsilyl, tert-butyldimethylsilyl, tert-butyldiethylsilyl), ($C_2$-$C_6$)alkenyl group (e.g., 1-allyl) and the like. These groups are optionally substituted by 1 to 3 substituents selected from a halogen atom (e.g., fluorine, chlorine, bromine, iodine), a ($C_1$-$C_6$)alkoxy group (e.g., methoxy, ethoxy, propoxy), a nitro group and the like.

Examples of the carboxy-protecting group include ($C_1$-$C_6$) alkyl group (e.g., methyl, ethyl, propyl, isopropyl, butyl, tert-butyl), ($C_7$-$C_{10}$)aralkyl group (e.g., benzyl), phenyl group, trityl group, silyl group (e.g., trimethylsilyl, triethylsilyl, dimethylphenylsilyl, tert-butyldimethylsilyl, tert-butyldiethylsilyl, tert-butyldiphenylsilyl), ($C_2$-$C_6$)alkenyl group (e.g., 1-allyl) and the like can be mentioned. These groups are optionally substituted by 1 to 3 substituents selected from a halogen atom (e.g., fluorine, chlorine, bromine, iodine), a ($C_1$-$C_6$)alkoxy group (e.g., methoxy, ethoxy, propoxy), a nitro group and the like.

Examples of the carbonyl-protecting group include cyclic acetal (e.g., 1,3-dioxane), acyclic acetal (e.g., di-($C_1$-$C_6$) alkylacetal) and the like.

These protecting groups can be removed by a method known per se, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilylhalide (e.g., trimethylsilyliodide, trimethylsilylbromide and the like) and the like, a reduction method and the like are used.

[Kit for Liquid Phase Synthesis of Peptide]

The present invention also provides a kit for liquid phase synthesis of peptide, which contains the compound of the present invention as an essential constituent component. The kit may contain, besides the compound of the present invention, other components necessary for liquid phase synthesis reaction of peptide, for example, various solvents used for the reaction, amino acid (or peptide) to be the starting material and the like. When desired, a manual of liquid phase synthesis of peptide using the compound of the present invention can also be attached.

EXAMPLES

Other features of the invention will become apparent in the course of the following descriptions of exemplary embodiments which are given for illustration of the invention and are not intended to be limiting thereof. The reagents, apparatuses and materials used in the present invention are commercially available unless otherwise specified. In the present specification, when amino acid and the like are indicated by abbreviation, each indication is based on the abbreviation of the IUPAC-IUB Commission on Biochemical Nomenclature or conventional abbreviations in the art.

Example 1

Synthesis of 4-(12'-docosyloxy-1'-dodecyloxy)-2-methoxybenzyl alcohol (i) 12-Docosyloxy-1-bromododecane (1.00 g, 1.74 mmol), 4-hydroxy-2-methoxybenzaldehyde (292 mg, 1.92 mmol) and potassium carbonate (361 mg, 2.61 mmol) were suspended in DMF (10 ml), and the suspension was stirred at 70° C. for 2 days. The reaction mixture was cooled to room temperature, extracted with chloroform (20 ml), and washed once with 1N hydrochloric acid (10 ml) and 3 times with water (10 ml). The combined organic layers were evaporated under reduced pressure, and the residue was precipitated with methanol (10 ml) to give 4-(12'-docosyloxy-1'-dodecyloxy)-2-methoxybenzaldehyde (1.05 g, 1.63 mmol, 93%).

$^1$H-NMR (300 MHz, CDCl$_3$) δ: 0.88 (3H, t, J=6.6 Hz, —OC$_{21}$H$_{42}$-Me), 1.15-1.65 (58H, br, Alkyl-H), 1.80 (2H, m, Ar—O—CH$_2$—CH$_2$—), 3.39 (4H, t, J=6.6 Hz, —C$_{11}$H$_{22}$—CH$_2$—O—CH$_2$—C$_{21}$H$_{43}$), 3.90 (3H, s, —OMe), 4.02 (2H, t, J=6.6 Hz, Ar—O—CH$_2$—), 6.44 (1H, d, J=1.8 Hz, Ph, C3-H), 6.54 (1H, dd, J=1.8, 8.7 Hz, Ph, C5-H), 7.79 (1H, d, J=8.7 Hz, Ph, C6-H), 10.28 (1H, s, Ar—CHO)

(ii) 4-(12'-Docosyloxy-1'-dodecyloxy)-2-methoxybenzaldehyde (1.02 g, 1.58 mmol) was suspended in THF-MeOH (10 ml+0.5 ml), sodium borohydride (80 mg, 2.11 mmol) was added, and the suspension was stirred at 50° C. overnight. 1N Hydrochloric acid was added dropwise to the reaction mixture to quench the reaction, and the mixture was extracted with chloroform (20 ml), and washed once with 1N hydrochloric acid (10 ml) and 3 times with water (10 ml). The solvent was evaporated, and the obtained residue was precipitated with methanol (10 ml) and washed with acetonitrile to give 4-(12'-docosyloxy-1'-dodecyloxy)-2-methoxybenzyl alcohol (972 mg, 1.50 mmol, 95%).

$^1$H-NMR (300 MHz, CDCl$_3$) δ: 0.88 (3H, t, J=6.6 Hz, —OC$_{21}$H$_{42}$-Me), 1.15-1.65 (58H, br, Alkyl-H), 1.77 (2H, m, Ar—O—CH$_2$—CH$_2$—), 2.10 (1H, t, J=6.3 Hz, —OH), 3.39 (4H, t, J=6.9 Hz, —C$_{11}$H$_{22}$—CH$_2$—O—CH$_2$—C$_{21}$H$_{43}$), 3.84 (3H, s, —OMe), 3.95 (2H, t, J=6.6 Hz, Ar—O—CH$_2$—), 4.61 (2H, d, J=6.3 Hz, benzyl-H), 6.43 (1H, dd, J=2.1, 8.1 Hz, Ph, C5-H), 6.47 (1H, d, J=2.1 Hz, Ph, C3-H), 7.14 (1H, d, J=8.1 Hz, Ph, C6-H)

Example 2

Synthesis of 4-(12'-docosyloxy-1'-dodecyloxy)-2-methoxybenzylamine

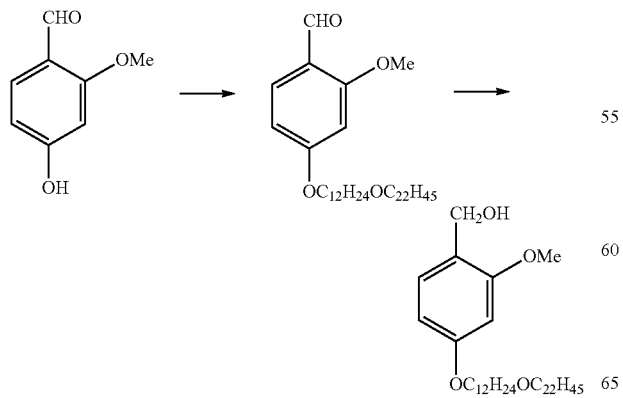

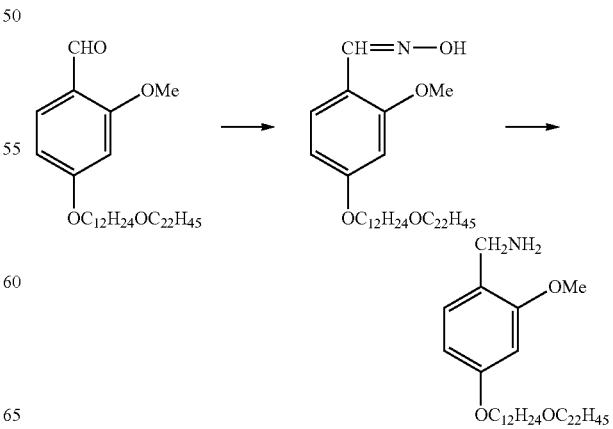

(i) 4-(12'-Docosyloxy-1'-dodecyloxy)-2-methoxybenzaldehyde (1.07 g, 1.66 mmol) was dissolved in dichloromethane (15 ml), hydroxylamine hydrochloride (344 mg, 4.80 mmol) and triethylamine (1.15 ml, 8.26 mmol) were added, and the mixture was stirred at room temperature. After confirmation of disappearance of the starting material, the solvent was evaporated under reduced pressure, and the residue was precipitated with acetonitrile to give 4-(12'-docosyloxy-1'-dodecyloxy)-2-methoxybenzaldoxime (1.08 g, 1.64 mmol, 98%).

$^1$H-NMR (300 MHz, CDCl$_3$) δ: 0.88 (3H, t, J=6.9 Hz, —C$_{21}$H$_{42}$-Me), 1.00-1.70 (58H, br, m, alkyl-H), 1.70-1.85 (2H, m, —O—CH$_2$—CH$_2$—C$_{20}$H$_{41}$), 3.39 (4H, t, J=6.7 Hz, —C$_{11}$H$_{22}$—CH$_2$—O—CH$_2$—C$_{21}$H$_{43}$), 3.83 (3H, s, —OMe), 3.97 (2H, t, J=6.5 Hz, Ar—O—CH$_2$—C$_{11}$H$_{22}$—), 6.44 (1H, d, J=2.0 Hz, C3-H), 6.48 (1H, dd, J=2.2, 8.6 Hz, C5-H), 7.03 (1H, br, —CHNOH), 7.62 (1H, d, J=8.5 Hz, C6-H), 8.41 (1H, s, —CHNOH)

(ii) To 4-(12'-docosyloxy-1'-dodecyloxy)-2-methoxybenzaldoxime (780 mg, 1.18 mmol) obtained in (i) were added THF (20 ml), methanol (10 ml) and 10% palladium-carbon (Pd/C, 80 mg), and the mixture was stirred under a hydrogen atmosphere overnight.

The reaction mixture was filtered to remove Pd/C, and the filtrate was concentrated under reduced pressure. The residue was precipitated with methanol to give 4-(12'-docosyloxy-1'-dodecyloxy)-2-methoxybenzylamine (744 mg, 1.15 mmol, 97%).

$^1$H-NMR (300 MHz, CDCl$_3$) δ: 0.88 (3H, t, J=6.9 Hz, —C$_{21}$H$_{42}$-Me), 1.00-1.90 (60H, br, m, alkyl-H), 3.39 (4H, t, J=6.9 Hz, —C$_{11}$H$_{22}$—CH$_2$—O—CH$_2$—C$_{21}$H$_{43}$), 3.78 (2H, s, Ar—CH$_2$—NH$_2$), 3.82 (3H, s, —OMe), 3.94 (2H, t, J=6.5 Hz, Ar—O—CH$_2$—C$_{11}$H$_{22}$—), 6.41 (1H, dd, J=2.2, 8.1 Hz, C5-H), 6.46 (1H, d, J=2.2 Hz, C3-H), 7.10 (1H, d, J=8.2 Hz, C6-H)

Example 3

Synthesis of 2-(12'-docosyloxy-1'-dodecyloxy)-4-methoxybenzyl alcohol

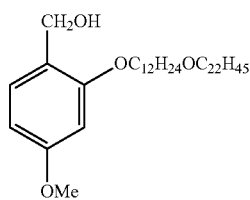

The title compound was synthesized from 2-hydroxy-4-methoxybenzaldehyde in the same manner as described for the synthesis in Example 1.

$^1$H-NMR (300 MHz, CDCl$_3$): δ0.88 (3H, t, J=6.6 Hz, —OC$_{21}$H$_{42}$-Me), 1.15-1.65 (58H, br, Alkyl-H), 1.81 (2H, m, Ar—O—CH$_2$—CH$_2$—), 2.21 (1H, br, s, —OH), 3.39 (4H, t, J=6.6 Hz, —C$_{11}$H$_{22}$—CH$_2$—O—CH$_2$—C$_{21}$H$_{43}$), 3.80 (3H, s, —OMe), 3.98 (2H, t, J=6.6 Hz, Ar—O—CH$_2$—), 4.61 (2H, br, d, J=3.6 Hz, benzyl-H), 6.44 (1H, dd, J=2.1, 8.1 Hz, Ph, C5-H), 6.45 (1H, s, Ph, C3-H), 7.16 (1H, d, J=7.8 Hz, Ph, C6-H)

Example 4

Synthesis of 4-(12'-docosyloxy-1'-dodecyloxy)benzyl alcohol

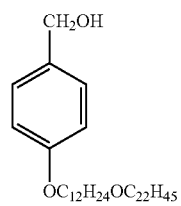

The title compound was synthesized from 4-hydroxybenzaldehyde in the same manner as described for the synthesis in Example 1.

$^1$H-NMR (300 MHz, CDCl$_3$): δ0.88 (3H, t, J=7.2 Hz, —OC$_{21}$H$_{42}$-Me), 1.15-1.65 (58H, br, Alkyl-H), 1.77 (2H, m, Ar—O—CH$_2$—CH$_2$—), 3.39 (4H, t, J=6.6 Hz, —C$_{11}$H$_{22}$—CH$_2$—O—CH$_2$—C$_{21}$H$_{43}$), 3.95 (2H, t, J=6.6 Hz, Ar—O—CH$_2$—), 4.61 (2H, d, J=4.8 Hz, benzyl-H), 6.88 (2H, d, J=8.4 Hz, Ph, C3, 5-H), 7.27 (2H, d, J=9.6 Hz, Ph, C2,6-H)

Example 5

Synthesis of 2-docosyloxy-4-methoxybenzyl alcohol

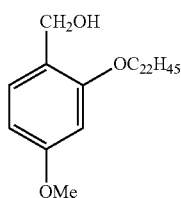

2-Hydroxy-4-methoxybenzaldehyde (5 g, 32.9 mmol), 1-bromodocosane (16.6 g, 42.7 mmol) and potassium carbonate (14.8 g, 107 mmol) were mixed with DMF (150 ml), and the mixture was stirred at 100° C. for 7 hr. Chloroform (400 ml) and 1N hydrochloric acid (300 ml) were added to the reaction mixture, and the mixture was washed. The organic layer was washed successively with 1N hydrochloric acid and saturated brine. The organic layer was concentrated and slurry-washed with methanol. The precipitate was collected by filtration and dried under reduced pressure. The obtained dried crystals were dissolved in THF (150 ml), sodium borohydride (3.7 g) was added, and the mixture was stirred at 40° C. for 3 hr. 1N Hydrochloric acid was added to the reaction mixture, and the mixture was concentrated. The mixture was extracted with chloroform, and washed successively with aqueous sodium hydrogen carbonate solution and saturated brine. The organic layer was concentrated. The obtained residue was washed with acetonitrile, and the precipitate was collected by filtration and dried under reduced pressure to give 2-docosyloxy-4-methoxybenzyl alcohol (9.8 g).

$^1$H-NMR (300 MHz, CDCl$_3$): δ0.88 (3H, t, J=6.5 Hz), 1.21-1.55 (38H, m), 1.76-1.85 (2H, m), 3.80 (3H, s), 3.98 (2H, t, J=6.3 Hz), 4.62 (2H, s), 6.42-6.42 (2H, m), 7.15 (1H, d, J=7.8 Hz)

Example 6

Synthesis of 4-methoxy-2-[3',4',5'-tris(octadecyloxy)benzyloxy]benzyl alcohol

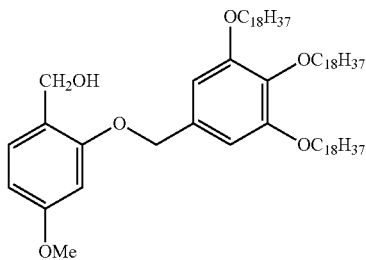

(i) 3,4,5-Tris(octadecyloxy)benzyl alcohol (83.0 g, 90.8 mmol) was dissolved in chloroform (830 ml), thionyl chloride (21.6 g, 0.182 mol) was added at 0° C., and the mixture was stirred at room temperature for 1.5 hr. The solvent was evaporated, and the residue was precipitated with acetonitrile (800 ml) to give 3,4,5-tri(octadecyloxy)benzylchloride (93.6 g) as wet crystals.

(ii) 3,4,5-Tri(octadecyloxy)benzylchloride (93.6 g, wet, <90.8 mmol), 2-hydroxy-4-methoxybenzaldehyde (15.2 g, 0.10 mol) and potassium carbonate (31.4 g, 0.23 mol) were suspended in DMF (830 ml), and the suspension was stirred at 80° C. overnight. The reaction mixture was dissolved in chloroform (1600 ml), and the mixture was washed 3 times with 1N hydrochloric acid (800 ml), once with 5% aqueous sodium hydrogen carbonate solution (800 ml), and once with 20% brine (800 ml). The solvent was evaporated, and the residue was precipitated with methanol (800 ml) and washed with acetonitrile (800 ml) to give 4-methoxy-2-[3',4',5'-tris(octadecyloxy)benzyloxy]benzaldehyde (93.5 g, 89.2 mmol, 98%).

(iii) 4-Methoxy-2-[3',4',5'-tris(octadecyloxy)benzyloxy]benzaldehyde (93.5 g, 89.2 mmol) was dissolved in THF-methanol (1870 ml+94 ml), and sodium borohydride (4.05 g, 107 mmol) was added at 0° C. After stirring at room temperature for 1.5 hr, 0.2N hydrochloric acid (100 ml) was added at 0° C. to quench the reaction. The solvent was evaporated to about half, and dissolved in chloroform (2400 ml). The mixture was washed twice with 0.1N hydrochloric acid (1200 ml), once with 5% aqueous sodium hydrogen carbonate solution (1200 ml), and once with 20% brine (1200 ml). The solvent was evaporated, and the residue was precipitated with methanol (900 ml) and washed with acetonitrile to give 4-methoxy-2-[3',4',5'-tris(octadecyloxy)benzyloxy]benzyl alcohol (92.4 g, 88.0 mmol, 97% yield vs 3,4,5-tris(octadecyloxy)benzyl alcohol).

$^1$H-NMR (300 MHz, CDCl$_3$): δ0.88 (9H, t, J=6.3 Hz, C$_{17}$H$_{34}$-Me), 1.15-1.40 (84H, br, C3',5'—OC$_3$H$_6$—C$_{14}$H$_{28}$—CH$_3$), 1.40-1.55 (6H, br, C3',4',5'-OC$_2$H$_4$—CH$_2$—C$_{15}$H$_{31}$), 1.70-1.85 (6H, m, C3',4',5'-OCH$_2$—CH$_2$—C$_{16}$H$_{33}$), 2.18 (1H, t, J=6.3 Hz, OH), 3.79 (3H, s, C4-OMe), 3.90-4.03 (6H, m, C3',4',5'-O—CH$_2$—C$_{17}$H$_{35}$), 4.65 (2H, d, J=6.6 Hz, Ar—CH$_2$—OH), 4.97 (2H, s, Ar—O—CH$_2$—Ar), 6.47 (1H, dd, J=2.1, 8.1 Hz, C5-H), 6.53 (1H, d, J=2.4 Hz, C3-H), 6.60 (2H, s, C2',6'-H), 7.19 (1H, d, J=8.1 Hz, C6-H)

Example 7

Synthesis of 2-[3',5'-di(docosyloxy)benzyloxy]-4-methoxybenzyl alcohol

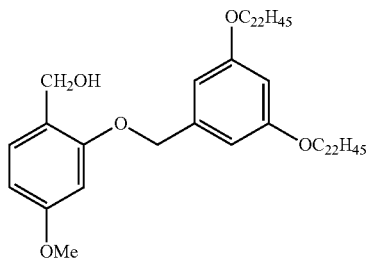

(i) 3,5-Di(docosyloxy)benzyl alcohol (500 mg, 0.66 mmol) was dissolved in chloroform (5 ml), thionyl chloride (71 µl, 0.99 mmol) and DMF (10 µl, 0.13 mmol) were added dropwise, and the mixture was stirred at room temperature for 1 hr. The solvent was evaporated, and the residue was precipitated with acetonitrile to give 3,5-di(docosyloxy)benzylchloride (505 mg, 0.65 mmol, 99%).

$^1$H-NMR (300 MHz, CDCl$_3$): δ0.88 (3H, t, J=6.6 Hz, —OC$_{21}$H$_{42}$-Me), 1.20-1.60 (76H, br, Alkyl-H), 1.76 (2H, m, Ar—O—CH$_2$—CH$_2$—), 3.93 (4H, t, J=6.6 Hz, Ar—O—CH$_2$—C$_{21}$H$_{43}$), 4.49 (2H, s, benzyl-H), 6.39 (1H, br, t, Ph, C4-H), 6.51 (2H, d, J=2.1 Hz, Ph, C2,6-H)

(ii) 3,5-Di(docosyloxy)benzylchloride (450 mg, 0.58 mmol), 2-hydroxy-4-methoxybenzaldehyde (185 mg, 1.22 mmol) and potassium carbonate (200 mg, 1.45 mmol) were suspended in DMF (4.5 ml), and the mixture was stirred at 80° C. for 6 hr. The reaction mixture was extracted with chloroform (20 ml), and washed 3 times with 1N hydrochloric acid (7 ml). The solvent was evaporated and the obtained residue was precipitated with methanol (5 ml) to give 2-[3',5'-di(docosyloxy)benzyl]-4-methoxybenzaldehyde (502 g, 0.56 mmol, 97%).

$^1$H-NMR (300 MHz, CDCl$_3$): δ0.88 (3H, t, J=6.6 Hz, —OC$_{21}$H$_{42}$-Me), 1.15-1.65 (76H, br, Alkyl-H), 1.76 (2H, m, Ar—O—CH$_2$—CH$_2$—), 3.84 (3H, s, —OMe), 3.93 (4H, t, J=6.6 Hz, Ar—O—CH$_2$—C$_{21}$H$_{43}$), 5.08 (2H, s, benzyl-H), 6.41 (1H, br, s, Ph, C3 or C5 or C4'-H), 6.49 (1H, d, J=2.1 Hz, Ph, C3 or C5 or C4'-H), 6.53-6.60 (3H, m, Ph, C2', C6'-H, C3 or C5 or C4'-H), 7.16 (1H, d, J=7.8 Hz, Ph, C6-H)

(iii) 2-(3',5'-Di(docosyloxy)benzyl)-4-methoxybenzaldehyde (450 mg, 0.50 mmol) was dissolved in THF-EtOH (4 ml+0.5 ml), sodium borohydride (34 mg, 0.90 mmol) was added, and the mixture was stirred for 3.5 hr. 1N Hydrochloric acid was added dropwise to the reaction mixture to quench the reaction, and the mixture was extracted with chloroform (15 ml), washed once with 1N hydrochloric acid (10 ml), and 3 times with water (5 ml). The solvent was evaporated, and the obtained residue was precipitated with methanol (5 ml) to give 2-(3',5'-di(docosyloxy)benzyl)-4-methoxybenzyl alcohol (424 mg, 0.47 mmol, 94%).

$^1$H-NMR (300 MHz, CDCl$_3$): δ0.88 (3H, t, J=6.6 Hz, —OC$_{21}$H$_{42}$-Me), 1.15-1.65 (76H, br, Alkyl-H), 1.76 (2H, m, Ar—O—CH$_2$—CH$_2$—), 3.79 (3H, s, —OMe), 3.95 (4H, t, J=6.6 Hz, Ar—O—CH$_2$—C$_{21}$H$_{43}$), 4.66 (2H, s, Ar—CH$_2$—OH), 5.00 (2H, s, Ar—CH$_2$—O—Ar), 6.40 (1H, br, t, Ph, C3 or C5 or C4'-H), 6.47 (1H, dd, J=2.1, 8.1 Hz, Ph, C3 or 05 or C4'-H), 6.50-6.60 (3H, m, Ph, C2',6'-H, C3 or C5 or C4'-H), 7.19 (1H, d, J=8.1 Hz, Ph, C6-H)

Example 8

Synthesis of 2-methoxy-4-[2',2',2'-tris(octadecyloxymethyl)ethoxy]benzyl alcohol

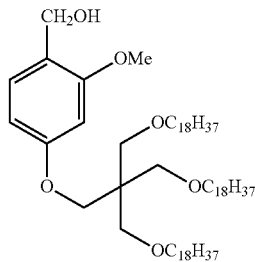

(i) To pentaerythritol (1.5 g, 11.0 mmol) were added DMF (100 ml), 1-bromooctadecane (11.4 g, 34.2 mmol) and sodium hydride (60 wt %, 1.54 g, 38.5 mmol), and the mixture was stirred at 100° C. for 22 hr. The reaction mixture was cooled to room temperature, chloroform (150 ml) was added, and 1N hydrochloric acid (150 ml) was added further dropwise. After stirring, the aqueous layer was removed, and the organic layer was further washed with 1N hydrochloric acid (100 ml) and water (100 ml). The organic layer was evaporated under reduced pressure, and the residue was precipitated with methanol (150 ml), and the obtained precipitate was washed with methanol (150 ml). The crude crystals were dried and purified by silica gel column chromatography (hexane:chloroform=1:1→hexane:ethyl acetate=10:1) to give 2,2,2-tris(octadecyloxymethyl)ethanol (2.21 g, 2.47 mmol, yield 23%).

$^1$H-NMR (300 MHz, CDCl$_3$): δ0.88 (3H, t, J=6.9 Hz, —OC$_{17}$H$_{34}$-Me), 1.10-1.65 (96H, br, C$_{18}$Alkyl-H), 3.12 (1H, t, J=6.0 Hz, OH), 3.38 (6H, t, J=6.3 Hz, —C—(CH$_2$—O—CH$_2$—C$_{17}$H$_{35}$)$_3$) 3.43 (6H, s, —C—(CH$_2$—O—C$_{18}$H$_{37}$)$_3$), 3.70 (2H, d, J=5.7 Hz, HO—CH$_2$—)

(ii) 2,2,2-Tris(octadecyloxymethyl)ethanol (500 mg, 560 μmol) was dissolved in toluene (10 ml), triphenylphosphine (294 mg, 1.12 mmol), imidazole (76.2 mg, 1.12 mmol) and iodine (284 mg, 1.12 mmol) were added, and the mixture was stirred at 100° C. overnight. The reaction mixture was cooled to room temperature, toluene (10 ml) was added, and the mixture was partitioned and washed three times with water (5 ml). The organic layer was evaporated under reduced pressure, and the residue was precipitated with acetonitrile (10 ml) to give 1-[3-iodo-2,2-bis(octadecyloxymethyl)propoxy]octadecane (555 mg, 553 μmol, yield 98%).

$^1$H-NMR (300 MHz, CDCl$_3$): δ0.88 (3H, t, J=6.9 Hz, —OC$_{17}$H$_{34}$-Me), 1.10-1.65 (96H, br, C18Alkyl-H), 3.33 (6H, s, —C—(CH$_2$—O—C$_{18}$H$_{37}$)$_3$), 3.38 (6H, t, J=6.3 Hz, —C—(CH$_2$—O—CH$_2$—C$_{17}$H$_{35}$)$_3$), 3.48 (2H, s, I—CH$_2$—)

(iii) 4-Hydroxy-2-methoxybenzaldehyde (136 mg, 894 μmol) was dissolved in DMF (10 ml), 1-[3-iodo-2,2-bis(octadecyloxymethyl)propoxy]octadecane (600 mg, 598 μmol) and potassium carbonate (165 mg, 1.19 mmol) were added, and the mixture was stirred at 130° C. for 3 days. The reaction mixture was cooled to room temperature, 1N hydrochloric acid (10 ml) and chloroform (10 ml) were added, and the mixture was stirred. The aqueous layer was removed, and the organic layer was further washed twice with purified water (10 ml). The organic layer was evaporated under reduced pressure, and the residue was precipitated with methanol to give crude crystals of 2-methoxy-4-[2',2',2'-tris(octadecyloxymethyl)ethoxy]benzaldehyde (592 mg, 96%). The obtained crude crystals were purified by silica gel column chromatography (chloroform-hexane=2:1-chloroform→hexane-ethyl acetate=10:1).

$^1$H-NMR (300 MHz, CDCl$_3$): δ0.88 (3H, t, J=6.9 Hz, —OC$_{17}$H$_{34}$-Me), 1.10-1.60 (96H, br, C18Alkyl-H), 3.38 (6H, t, J=6.3 Hz, —C—(CH$_2$—O—CH$_2$—C$_{17}$H$_{35}$)$_3$), 3.48 (6H, s, —C—(CH$_2$—O—C$_{18}$H$_{37}$)$_3$), 3.90 (3H, s, —OMe), 4.03 (2H, s, Ar—O—CH$_2$—), 6.43 (1H, d, J=2.1 Hz, Ph C3-H), 6.57 (1H, dd, J=2.1, 9.0 Hz, Ph C5-H), 7.78 (1H, d, J=9.0 Hz, Ph C6-H), 10.28 (1H, s, Ar—CHO)

(iv) 2-Methoxy-4-(2',2',2'-tris(octadecyloxymethyl)ethoxy)benzaldehyde (288 mg, 280 μmol) was dissolved in THF (3 ml), methanol (0.3 ml) and sodium borohydride (31.8 mg, 841 μmol) were added, and the mixture was stirred at 60° C. for 2 hr. The reaction mixture was cooled to room temperature, 1N hydrochloric acid (5 ml) and chloroform (5 ml) were added, and the mixture was stirred. The aqueous layer was removed, and the organic layer was further washed twice with purified water (5 ml). The organic layer was evaporated under reduced pressure, and the residue was azeotropically distilled with acetonitrile and dried in vacuo to give 2-methoxy-4-(2',2',2'-tris(octadecyloxymethyl)ethoxy)benzyl alcohol.

$^1$H-NMR (300 MHz, CDCl$_3$): δ0.88 (3H, t, J=6.6 Hz, —OC$_{17}$H$_{34}$-Me), 1.10-1.60 (96H, br, C18Alkyl-H), 2.09 (1H, br, OH), 3.38 (6H, t, J=6.3 Hz, —C—(CH$_2$—O—CH$_2$—CH$_{17}$H$_{35}$)$_3$), 3.48 (6H, s, —C—(CH$_2$—O—C$_{18}$H$_{37}$)$_3$), 3.85 (3H, s, —OMe), 3.95 (2H, s, Ar—O—CH$_2$—), 4.60 (1H, d, J=5.1 Hz, benzyl-H), 6.40-6.55 (2H, m, Ph C3, 5-H), 6.57 (1H, dd, J=2.1, 9.0 Hz, Ph C5-H), 7.12 (1H, d, J=8.7 Hz, Ph C6-H)

Example 9

Synthesis of 2-methoxy-4-[2',2',2'-tris(octadecyloxymethyl)ethoxy]benzylamine

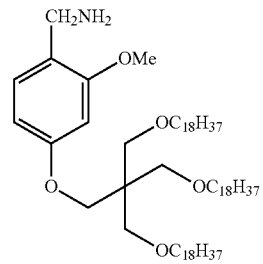

(i) 2-Methoxy-4-[2',2',2'-tris(octadecyloxymethyl)ethoxy]benzaldehyde (50 mg, 0.049 mmol) was dissolved in dichloromethane (1 ml), hydroxylamine hydrochloride (18 mg, 0.26 mmol) and triethylamine (51 μl, 0.37 mmol) were added, and the mixture was stirred at room temperature for 4 hr. The solvent was evaporated, and the residue was precipitated with acetonitrile to give 2-methoxy-4-[2,2,2-tris(octadecyloxymethyl)ethoxy]benzaldoxime (43 mg, 0.041 mmol, 85%).

$^1$H-NMR (300 MHz, CDCl$_3$): δ0.88 (3H, t, J=6.9 Hz, —OC$_{17}$H$_{34}$-Me), 1.10-1.60 (96H, br, C18Alkyl-H), 3.38 (6H, t, J=6.3 Hz, —C—(CH$_2$—O—CH$_2$—C$_{17}$H$_{35}$)$_3$) 3.48 (6H, s, —C—(CH$_2$—O—C$_{18}$H$_{37}$)$_3$) 3.83 (3H, s, —OMe), 3.98 (2H, s, Ar—O—CH$_2$—), 6.43 (1H, d, J=2.1 Hz, Ph C3-

H), 6.52 (1H, dd, J=2.1, 8.7 Hz, Ph C5-H), 6.94 (1H, br, N—O H), 7.61 (1H, d, J=8.7 Hz, Ph C6-H), 8.41 (1H, s, —CH=N—)

(ii) 2-Methoxy-4-[2',2',2'-tris(octadecyloxymethyl)ethoxy]benzaldoxime (40 mg, 0.038 mmol) was dissolved in THF (1 ml), diisobutylaluminum hydride (DIBAL)-toluene solution (127 µl, 0.13 mmol) was added dropwise, and the mixture was stirred for 2.5 hr. 1N Hydrochloric acid (2 ml) was added dropwise to the reaction mixture to quench the reaction, and the mixture was extracted with chloroform (2 ml) and washed with 10% aqueous sodium carbonate solution (1 ml). The solvent was evaporated, and acetonitrile (1 ml) was added to the residue. The precipitate was collected by filtration, and purified by silica gel chromatography to give 2-methoxy-4-[2',2',2'-tris(octadecyloxymethyl)ethoxy]benzylamine (43 mg, 0.041 mmol, 85%).

$^1$H-NMR (300 MHz, CDCl$_3$): δ0.88 (3H, t, J=6.9 Hz, —OC$_{17}$H$_{34}$-Me), 1.10-1.60 (96H, br, C18Alkyl-H), 2.82 (2H, d, J=5.4 Hz, —NH$_2$), 3.38 (6H, t, J=6.3 Hz, —C—(CH$_2$—O—CH$_2$—C$_{17}$H$_{35}$)$_3$), 3.48 (6H, s, —C—(CH$_2$—O—C$_{18}$H$_{37}$)$_3$), 3.82 (3H, s, —OMe), 3.70-4.00 (2H, m, Ar—O—CH$_2$—, benzyl-H), 6.40-6.50 (3H, m, Ph C3,5,6-H)

Example 10

Synthesis of 4-methoxy-2-[3',4',5'-tris(octadecyloxy)cyclohexylmethyloxy]benzyl alcohol

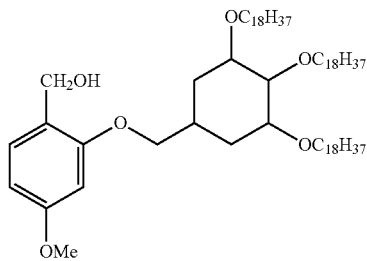

(i) To methyl 3,4,5-tris(octadecyloxy)benzoate (1 g, 10.6 mmol) was added cyclohexane, 5% rhodium-carbon (0.8 g) was added, and hydrogenation was performed at 80° C., 10 atm. Tetrahydrofuran (10 ml) was added, and the catalyst was filtered off. The filtrate was concentrated, methanol (8 ml) was added, and the mixture was stirred. The precipitate was collected by filtration and dried to give methyl 3,4,5-tris(octadecyloxy)cyclohexylcarboxylate (820 mg, 0.87 mmol, 82%).

$^1$H-NMR (300 MHz, CDCl$_3$): δ0.89 (9H, t, J=6.9 Hz, C$_{17}$H$_{34}$-Me), 1.25-1.44 (90H, m), 1.52-1.60 (6H, m), 1.86-1.94 (4H, m), 2.23 (1H, m), 3.09-3.14 (2H, m), 3.41-3.47 (4H, m), 3.64-3.68 (5H, m), 3.86 (1H, s)

(ii) Methyl 3,4,5-tris(octadecyloxy)cyclohexylcarboxylate (70.0 g, 73.9 mmol) was dissolved in THF (1050 ml), and DIBAL (1.0 mol/L toluene solution, 200 ml, 200 mmol) was added dropwise at 0° C. over 40 min under a nitrogen atmosphere. After stirring at room temperature for 2 hr, 0.2N hydrochloric acid (50 ml) was added dropwise at 0° C. to quench the reaction. The solvent was evaporated to about half, and the residue was dissolved in chloroform (700 ml). The mixture was washed three times with 1N hydrochloric acid (300 ml), once with 5% aqueous sodium hydrogen carbonate solution (300 ml), and once with 20% brine (300 ml). The solvent was evaporated, and the residue was precipitated with methanol (700 ml), and washed with acetonitrile to give 3,4,5-tris(octadecyloxy)cyclohexylmethyl alcohol (68.2 g, 74.2 mmol, 100%).

$^1$H-NMR (300 MHz, CDCl$_3$): δ0.88 (9H, t, J=6.9 Hz, C$_{17}$H$_{34}$-Me), 1.15-1.80 (101H, br, m, C1-H, C2,6-H$_2$, C3,4,5-OCH$_2$—C$_{16}$H$_{32}$—CH$_3$), 3.10-3.20 (2H, br, m, C3,5-H), 3.35-3.60 (6H, m, C3,5-O—CH$_2$—C$_{17}$H$_{35}$, Cy-CH$_2$—OH), 3.67 (2H, t, J=6.6 Hz, C4-O—CH$_2$—C$_{17}$H$_{35}$), 3.90 (1H, s, C4-H)

(iii) 3,4,5-Tris(octadecyloxy)cyclohexylmethyl alcohol (68.5 g, 74.5 mmol) was dissolved in chloroform (700 ml), pyridine (26.9 ml, 0.33 mol), DMAP (903 mg, 7.39 mmol) and p-toluenesulfonyl chloride (44.9 g, 0.236 mol) were added, and the mixture was stirred for 5 days. The solvent was evaporated, and the residue was precipitated with acetonitrile (700 ml) and washed with acetonitrile (700 ml) to give 3,4,5-tris(octadecyloxy)cyclohexylmethyl tosylate (76.9 g, 71.6 mmol, 96%).

$^1$H-NMR (300 MHz, CDCl$_3$): δ0.88 (9H, t, J=6.9 Hz, C$_{17}$H$_{34}$-Me), 1.15-1.80 (101H, br, m, C1-H, C2,6-H$_2$—, C3,4,5-OCH$_2$—C$_{16}$H$_{32}$—CH$_3$), 2.45 (3H, s, Me(Ts)), 3.05-3.12 (2H, br, m, C3,5-H), 3.30-3.55 (4H, m, C3,5-O—CH$_2$—C$_{17}$H$_{35}$), 3.62 (2H, t, J=6.6 Hz, C4-O—CH$_2$—C$_{17}$H$_{35}$), 3.80-3.90 (3H, m, C4-H, Cy-CH$_2$—OTs), 7.34 (2H, d, J=8.1 Hz, C2',6'-H), 7.78 (2H, d, J=8.4 Hz, C3',5'-H)

(iv) 3,4,5-Tris(octadecyloxy)cyclohexylmethyl tosylate (76.9 g, 71.6 mmol), 2-hydroxy-4-methoxybenzaldehyde (16.9 g, 0.11 mol) and potassium carbonate (25.6 g, 0.18 mol) were suspended in DMF (700 ml), and the mixture was stirred at 80° C. overnight.

The reaction mixture was dissolved in chloroform (700 ml), washed twice with 0.5N hydrochloric acid (300 ml), once with 5% aqueous sodium hydrogen carbonate solution (300 ml), and once with pure water (300 ml). The solvent was evaporated, and the residue was precipitated with methanol (700 ml) to give 4-methoxy-2-[3',4',5'-tris(octadecyloxy)cyclohexylmethyloxy]benzaldehyde (73.56 g, 69.8 mmol, 97%).

$^1$H-NMR (300 MHz, CDCl$_3$): δ0.88 (9H, t, J=6.9 Hz, C$_{17}$H$_{34}$-Me), 1.15-1.90 (101H, br, m, C1'-H, C2',6'-H$_2$, C3',4',5'-OCH$_2$—C$_{16}$H$_{32}$—CH$_3$), 3.15-3.25 (2H, br, m, C3',5'-H), 3.35-3.55 (4H, m, C3',5'-O—CH$_2$—C$_{17}$H$_{35}$), 3.68 (2H, t, J=6.6 Hz, C4'-O—CH$_2$—C$_{17}$H$_{35}$), 3.87 (3H, s, C4-OMe), 3.90 (2H, d, J=6.0 Hz, Cy-CH$_2$—OAr), 3.95 (1H, s, C4'-H), 6.41 (1H, d, J=2.1 Hz, C3-H), 6.54 (1H, dd, J=1.5, 8.7 Hz, C5-H), 7.81 (1H, d, J=8.7 Hz, C6-H), 10.35 (1H, s, CHO)

(v) 4-Methoxy-2-(3',4',5'-tris(octadecyloxy)cyclohexylmethyloxy)benzaldehyde (73.56 g, 69.8 mmol) was dissolved in THF-methanol (1100 ml+55 ml), and sodium borohydride (3.17 g, 83.8 mmol) was added at 0° C. After stirring the mixture at room temperature for 1.5 hr, 0.2N hydrochloric acid (150 ml) was added at 0° C. to quench the reaction. The solvent was evaporated to about half, and the residue was dissolved in chloroform (1400 ml), washed twice with 0.1N hydrochloric acid (700 ml), and twice with pure water (700 ml). The solvent was evaporated, and the residue was precipitated with methanol (800 ml), and washed with acetonitrile (800 ml) to give 4-methoxy-2-(3',4',5'-tris(octadecyloxy)cyclohexylmethyloxy)benzyl alcohol (71.5 g, 67.7 mmol, 92% vs methyl 3,4,5-tris(octadecyloxy)cyclohexylcarboxylate).

$^1$H-NMR (300 MHz, CDCl$_3$): δ0.88 (9H, t, J=6.9 Hz, C$_{17}$H$_{34}$-Me), 1.15-1.45 (101H, br, m, C1'-H, C2',6'-H$_2$, C3',4',5'-OCH$_2$—C$_{16}$H$_{32}$—CH$_3$), 2.10 (1H, t, J=6.3 Hz, OH), 3.18 (1H, br, d, J=10.2 Hz, C3',5'-H), 3.37-3.57 (4H, m, C3',5'-O—CH$_2$—C$_{17}$H$_{35}$), 3.68 (2H, t, J=6.6 Hz, C4'-O—CH$_2$—C$_{17}$H$_{35}$), 3.80 (3H, s, C4-Me), 3.86 (2H, d, J=5.7 Hz,

Cy-CH₂—OAr), 3.94 (1H, s, C4'-H), 4.62 (2H, d, J=6.3 Hz, Ar—CH₂—OH), 6.39-6.49 (2H, m, C3-H, C5-H), 7.17 (1H, d, J=8.4 Hz, C6-H)

Example 11

Synthesis of 2-methoxy-4-[3',4',5'-tris(octadecyloxy) cyclohexylmethyloxy]benzyl alcohol

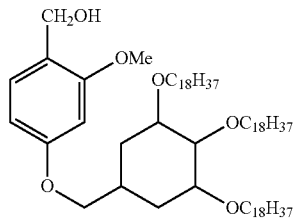

(i) 3,4,5-Tris(octadecyloxy)cyclohexylmethyl alcohol (238 mg, 0.26 mmol), 4-hydroxy-2-methoxybenzaldehyde (79 mg, 0.52 mmol) and triphenylphosphine (149 mg, 0.57 mmol) were dissolved in THF (6 ml), diisopropyl azodicarboxylate (115 mg, 0.57 mmol) was added, and the mixture was stirred for 5.5 hr. Water (1 ml) was added to the reaction mixture and the mixture was concentrated. The residue was precipitated with acetonitrile (2.5 ml) to give 2-methoxy-4-[3',4',5'-tris(octadecyloxy)cyclohexylmethyloxy]benzaldehyde (272 mg, 0.26 mmol, 100%).

¹H-NMR (300 MHz, CDCl₃): δ0.88 (9H, t, J=6.9 Hz, C₁₇H₃₄-Me), 1.15-1.90 (101H, br, m, C1'-H, C2',6'-H₂, C3', 4',5'—OCH₂—C₁₆H₃₂—CH₃), 3.18 (2H, d, J=10.2 Hz, C3',5'-H), 3.35-3.55 (4H, m, C3',5'-O—CH₂—C₁₇H₃₅), 3.68 (2H, t, J=6.7 Hz, C4'-O—CH₂—C₁₇H₃₅), 3.75-4.00 (3H, m, Cy-CH₂—OAr, C4'-H), 3.90 (3H, s, C4-OMe), 6.42 (1H, d, J=1.6 Hz, C3-H), 6.51 (1H, d, J=8.7 Hz, C5-H), 7.79 (1H, d, J=8.6 Hz, C6-H), 10.28 (1H, s, CHO)

(ii) 2-Methoxy-4-[3',4',5'-tris(octadecyloxy)cyclohexylmethyloxy]benzaldehyde (272 mg, 0.26 mmol) was suspended in chloroform-methanol (6 ml+0.5 ml), and sodium borohydride (29 mg, 0.77 mmol) was added. After stirring at 60° C. overnight, the mixture was dissolved in chloroform (12 ml), and washed with 0.5N hydrochloric acid (8 ml) and pure water (8 ml). The solvent was evaporated, and the residue was precipitated with acetonitrile (2.5 ml) to give 2-methoxy-4-[3',4',5'-tris(octadecyloxy)cyclohexylmethyloxy]benzyl alcohol (260 mg, 0.25 mmol, 95%).

¹H-NMR (300 MHz, CDCl₃): δ0.88 (9H, t, J=6.9 Hz, C₁₇H₃₄-Me), 1.15-1.45 (101H, br, m, C1'-H, C2',6'-H₂, C3', 4',5'-OCH₂—C₁₆H₃₂—CH₃), 2.11 (1H, t, J=5.9 Hz, OH), 3.18 (2H, br, d, J=10.3 Hz, C3',5'-H), 3.35-3.57 (4H, m, C3',5'-O—CH₂—C₁₇H₃₅), 3.68 (2H, t, J=6.7 Hz, C4'-O—CH₂—C₁₇H₃₅), 3.75-3.90 (2H, m, Cy-CH₂—OAr), 3.84 (3H, s, C4-OMe), 3.93 (1H, s, C4'-H), 4.60 (2H, d, J=5.5 Hz, Ar—CH₂—OH), 6.38-6.50 (2H, m, C3-H, C5-H), 7.13 (1H, d, J=8.2 Hz, C6-H)

Example 12

Synthesis of 3,5-dimethoxy-4-[3',4',5'-tris(octadecyloxy)cyclohexylmethyloxy]benzyl alcohol

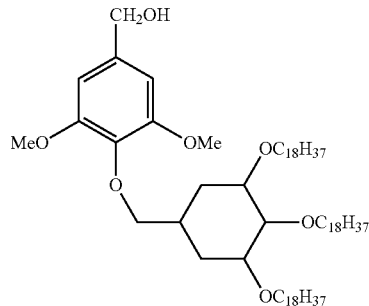

(i) 3,4,5-Tris(octadecyloxy)cyclohexylmethyltosylate (103 mg, 0.10 mmol), 4-hydroxy-3,5-dimethoxybenzaldehyde (28 mg, 0.15 mmol) and potassium carbonate (32 mg, 0.23 mmol) were suspended in DMF (1 ml), and the suspension was stirred at 80° C. overnight. The reaction mixture was dissolved in chloroform (5 ml), washed twice with 0.5N hydrochloric acid (3 ml), once with 5% aqueous sodium hydrogen carbonate solution (3 ml), and once with pure water (3 ml). The solvent was evaporated, and the residue was precipitated with methanol (10 ml) to give 4-[3',4',5'-tris(octadecyloxy)cyclohexylmethyloxy]-3,5-dimethoxybenzaldehyde (73 mg, 0.07 mmol, yield 70%).

¹H-NMR (300 MHz, CDCl₃): δ0.88 (9H, t, J=6.6 Hz), 1.15-1.80 (99H, br, m), 3.18-3.21 (2H, m), 3.43-3.49 (4H, m), 3.69 (2H, t, J=6.7 Hz), 3.78-3.87 (9H, m), 6.05 (2H, s), 10.34 (1H, s)

(ii) 4-[3',4',5'-Tris(octadecyloxy)cyclohexylmethyloxy]-3,5-dimethoxybenzaldehyde (73 mg, 0.07 mmol) was dissolved in THF (2 ml), 4 equivalents of sodium borohydride was added, and the mixture was stirred at 40° C. for 3 hr. The solvent was evaporated, and chloroform was added. The mixture was washed successively with 1N hydrochloric acid, aqueous sodium hydrogen carbonate solution and saturated brine. The solvent of the organic layer was evaporated, and acetonitrile was added. The precipitate was collected by filtration and dried to give 3,5-dimethoxy-4-[3',4',5'-tris(octadecyloxy)cyclohexylmethyloxy]benzyl alcohol (70 mg, 0.06 mmol).

¹H-NMR (300 MHz, CDCl₃): δ0.88 (9H, t, J=6.6 Hz), 1.15-1.80 (99H, br, m), 3.18-3.21 (2H, m), 3.43-3.50 (4H, m), 3.69 (2H, t, J=6.7 Hz), 3.78-3.87 (9H, m), 4.69 (2H, m), 6.03 (2H, s)

Example 13

Synthesis of N-(4-hydroxymethyl-3-methoxyphenyl) 3,4,5-tris(octadecyloxy)cyclohexylcarboxamide

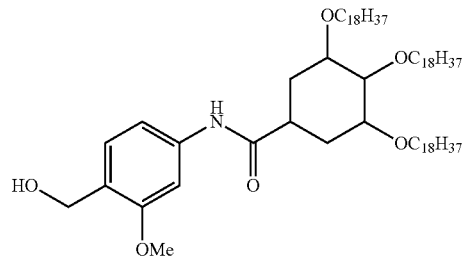

(i) Methyl 4-amino-2-methoxybenzoate (79 mg, 0.44 mmol) was dissolved in chloroform (1 ml), and HOBt (7 mg, 0.05 mmol) and 3,4,5-tris(octadecyloxy)cyclohexylcarboxylic acid (201 mg, 0.22 mmol) were added. EDC.HCl (45 mg, 0.23 mmol) was added under ice-cooling, and the mixture was stirred at room temperature overnight. After completion of the reaction, the solvent was evaporated, and the residue was precipitated with acetonitrile (10 ml), and then purified by silica gel column chromatography (chloroform/ethyl acetate=10:1) to give N-(3-methoxy-4-methoxycarbonylphenyl) 3,4,5-tris(octadecyloxy)cyclohexylcarboxamide (70 mg, 0.06 mmol, yield 27%).

$^1$H-NMR (300 MHz, CDCl$_3$): δ0.88 (9H, t, J=6.6 Hz), 1.15-1.80 (99H, m), 3.19-3.22 (2H, m), 3.39-3.49 (4H, m), 3.69 (2H, t, J=6.7 Hz), 3.7 (1H, br, s), 3.83 (3H, s), 3.92 (3H, s), 6.82 (1H, d, J=6.0 Hz), 7.36 (1H, s), 7.63 (1H, s), 7.81 (1H, d, J=6.0 Hz)

(ii) N-(3-Methoxy-4-methoxycarbonylphenyl) 3,4,5-tris(octadecyloxy)cyclohexylcarboxamide (70 mg, 0.06 mmol) was dissolved in dehydrated THF (1 ml), 1M DIBAL/toluene (0.2 ml, 0.012 mmol) was added dropwise, and the mixture was stirred for 5 hr. After completion of the reaction, 1N hydrochloric acid was added to quench the reaction, and the mixture was extracted with chloroform (5 ml) and washed with 1N hydrochloric acid (3 ml). The solvent was evaporated and the residue was precipitated with methanol (10 ml) and slurry-washed with acetonitrile (5 ml) and 1N hydrochloric acid (5 ml) to give N-(4-hydroxymethyl-3-methoxyphenyl) 3,4,5-tris(octadecyloxy)cyclohexylcarboxamide (60 mg, 0.06 mmol, yield 100%).

$^1$H-NMR (300 MHz, CDCl$_3$): δ0.88 (9H, t, J=6.6 Hz), 1.15-1.80 (99H, m), 3.19-3.22 (2H, m), 3.39-3.49 (4H, m), 3.69 (2H, t, J=6.7 Hz), 3.88-3.92 (4H, m), 4.63 (2H, s), 6.77 (1H, d, J=6.0 Hz), 7.18 (1H, d, J=6.0 Hz), 7.51 (1H, s), 7.61 (1H, s)

Example 14

Synthesis of N-(5-hydroxymethyl-2-methoxyphenyl) 3,4,5-tris(octadecyloxy)cyclohexylcarboxamide

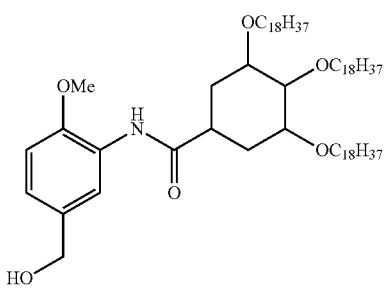

(i) Methyl 3-amino-4-methoxybenzoate (81 mg, 0.44 mmol) was dissolved in chloroform (1 ml), HOBt (7 mg, 0.05 mmol) and 3,4,5-tris(octadecyloxy)cyclohexylcarboxylic acid (199 mg, 0.22 mmol) were added. EDC.HCl (45 mg, 0.23 mmol) was added under ice-cooling, and the mixture was stirred at room temperature overnight. After completion of the reaction, the solvent was evaporated, and the residue was precipitated with acetonitrile (10 ml) to give N-(2-methoxy-5-methoxycarbonylphenyl) 3,4,5-tris(octadecyloxy)cyclohexylcarboxamide (225 mg, 0.21 mmol, yield 95%).

$^1$H-NMR (300 MHz, CDCl$_3$): δ0.88 (9H, t, J=6.6 Hz), 1.15-1.80 (99H, m), 3.19-3.22 (2H, m), 3.39-3.49 (4H, m), 3.69 (2H, t, J=6.7 Hz), 3.73 (1H, br, s), 3.88 (3H, s), 3.94 (3H, s), 6.91 (1H, d, J=6.0 Hz), 7.79-86 (2H, m), 7.63 (1H, s)

(ii) N-(2-Methoxy-5-methoxycarbonylphenyl) 3,4,5-tris(octadecyloxy)cyclohexylcarboxamide (225 mg, 0.21 mmol) was dissolved in dehydrated THF (2.5 ml), 1M DIBAL/toluene (0.6 ml, 0.6 eq) was added dropwise, and the mixture was stirred for 5 hr. After completion of the reaction, 1N hydrochloric acid was added to quench the reaction, and the mixture was extracted with chloroform (10 ml), and washed with 1N hydrochloric acid (5 ml). The solvent was evaporated and the residue was precipitated with methanol (15 ml) and slurry-washed with acetonitrile (10 ml) and 1N hydrochloric acid (10 ml) to give N-(5-hydroxymethyl-2-methoxyphenyl) 3,4,5-tris(octadecyloxy)cyclohexylcarboxamide (200 mg, 0.18 mmol, yield 86%).

$^1$H-NMR (300 MHz, CDCl$_3$): δ0.88 (9H, t, J=6.6 Hz), 1.15-1.80 (99H, m), 3.19-3.22 (2H, m), 3.39-3.49 (4H, m), 3.69 (2H, t, J=6.7 Hz), 3.83-3.94 (4H, m), 4.59 (2H, m), 6.86 (1H, d, J=6.0 Hz), 7.07 (1H, d, J=6.0 Hz), 7.90 (1H, s), 8.37 (1H, s)

Example 15

Synthesis of N-(4-hydroxymethylphenyl) 3,4,5-tris(octadecyloxy)cyclohexylcarboxamide

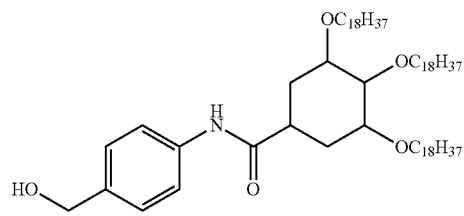

4-Aminobenzyl alcohol (282 mg, 2.29 mmol) was dissolved in chloroform (40 ml), and HOBt (32 mg, 0.23 mmol) and 3,4,5-tris(octadecyloxy)cyclohexylcarboxylic acid (1.11 g, 1.19 mmol) were added. EDC.HCl (356 mg, 1.86 mmol) and pure water (120 μl) were added under ice-cooling, and the mixture was stirred at room temperature overnight. After completion of the reaction, the solvent was evaporated, and the residue was precipitated with acetonitrile (10 ml), and isolated by silica gel column chromatography (chloroform/ethyl acetate=10:1) to give N-(4-hydroxymethylphenyl) 3,4,5-tris(octadecyloxy)cyclohexylcarboxamide (556 mg, 0.54 mmol, yield 45%).

$^1$H-NMR (300 MHz, CDCl$_3$): δ0.87 (9H, t, J=6.6 Hz), 1.12-1.83 (99H, m), 3.20-3.24 (2H, m), 3.38-3.45 (4H, m), 3.69 (2H, t, J=6.7 Hz), 3.88-3.92 (1H, m), 4.63 (2H, s), 7.27 (2H, d, J=6.0 Hz), 7.59 (2H, d, J=6.0 Hz), 8.01 (1H, s)

Example 16

Condensation of 4-(12'-docosyloxy-1'-dodecyloxy)-2-methoxybenzyl alcohol with Fmoc-Cys(Trt)-OH 4-(12'-Docosyloxy-1'-dodecyloxy)-2-methoxybenzyl alcohol (300 mg, 0.46 mmol), Fmoc-Cys(Trt)-OH (326 mg, 0.56 mmol) and DMAP (11 mg, 0.090 mmol) were dissolved in chloroform (6 ml), EDC.HCl (116 mg, 0.61 mmol) was added at 0° C., and the mixture was stirred at room temperature for 2.5 hr. The solvent was evaporated, and the residue was precipitated with methanol to give a condensed product (586 mg, 0.48 mmol, 100%).

¹H-NMR (300 MHz, CDCl₃): δ0.88 (3H, t, J=6.8 Hz, —OC₂₁H₄₂-Me), 1.15-1.65 (58H, br, Alkyl-H), 1.76 (2H, m, Ar—OCH₂—CH₂—), 2.50-2.70 (2H, m, S—CH₂—), 3.39 (4H, t, J=6.7 Hz, —C₁₁H₂₂—CH₂—O—CH₂—C₂₁H₄₃), 3.71 (3H, s, OMe), 3.91 (2H, t, J=6.2 Hz, Ar—O—CH₂—), 4.15-4.25 (1H, m, fluorene C9-H), 4.25-4.40 (3H, m, fluorene-CH₂—O—, Cys α-H), 5.13 (2H, d, J=2.9 Hz, benzyl-H), 5.27 (1H, d, J=8.3 Hz, Fmoc-NH—), 6.35-6.45 (2H, m, Ph C3,5-H), 7.10-7.45 (21H, m, C2,6-H, fluorene C2,3,6,7-H, Trt), 7.59 (2H, d, J=7.4 Hz, fluorene C1,8-H), 7.76 (2H, d, J=7.0 Hz, fluorene C4,5-H)

Example 17

Condensation of 2-(12'-docosyloxy-1'-dodecyloxy)-4-methoxybenzyl alcohol with Fmoc-Cys(Trt)-OH The title compound was synthesized from 2-(12'-docosyloxy-1'-dodecyloxy)-4-methoxybenzyl alcohol in the same manner as described in Example 16.

¹H-NMR (300 MHz, CDCl₃): δ0.88 (3H, t, J=6.9 Hz, —OC₂₁H₄₂-Me), 1.15-1.65 (58H, br, Alkyl-H), 1.76 (2H, m, Ar—O—CH₂—CH₂—), 2.50-2.70 (2H, m, S—CH₂—), 3.38 (4H, t, J=6.7 Hz, —C₁₁H₂₂—CH₂—O—CH₂—C₂₁H₄₃), 3.78 (3H, s, OMe), 3.86 (2H, t, J=6.5 Hz, Ar—O—CH₂—), 4.15-4.25 (1H, m, fluorene C9-H), 4.25-4.35 (3H, m, fluorene-CH₂—O—, Cys α-H), 5.16 (2H, s, benzyl-H), 5.28 (1H, d, J=8.1 Hz, Fmoc-NH—), 6.35-6.43 (2H, m, Ph C3,5-H), 7.10-7.45 (21H, m, C2,6-H, fluorene C2,3,6,7-H, Trt), 7.59 (2H, d, J=7.6 Hz, fluorene C1,8-H), 7.76 (2H, d, J=6.9 Hz, fluorene C4,5-H)

Example 18

Condensation of 4-(12'-docosyloxy-1'-dodecyloxy)benzyl alcohol with Fmoc-Cys(Trt)-OH The title compound was synthesized from 4-(12'-docosyloxy-1'-dodecyloxy)benzyl alcohol in the same manner as described in Example 16.

¹H-NMR (300 MHz, CDCl₃): δ0.88 (3H, t, J=6.9 Hz, —OC₂₁H₄₂-Me), 1.15-1.65 (58H, br, Alkyl-H), 1.76 (2H, m, Ar—O—CH₂—CH₂—), 2.50-2.70 (2H, m, S—CH₂—), 3.39 (4H, t, J=6.6 Hz, —C₁₁H₂₂—CH₂—O—CH₂—C₂₁H₄₃), 3.90 (2H, t, J=6.2 Hz, Ar—O—CH₂—), 4.15-4.25 (1H, m, fluorene C9-H), 4.25-4.35 (3H, m, fluorene-CH₂—O—, Cys α-H), 5.08 (2H, s, benzyl-H), 5.26 (1H, d, J=8.3 Hz, Fmoc-NH—), 6.82 (2H, d, J=8.4 Hz, Ph, C3,5-H), 7.15-7.45 (21H, m, C2,6-H, fluorene C2,3,6,7-H, Trt), 7.59 (2H, d, J=7.5 Hz, fluorene C1,8-H), 7.76 (2H, d, J=7.4 Hz, fluorene C4,5-H)

Example 19

Condensation of 4-methoxy-2-(3',4',5'-tris(octadecyloxy)benzyloxy)benzyl alcohol with Fmoc-Cys(Trt)-OH The title compound was synthesized from 4-methoxy-2-(3',4',5'-tris(octadecyloxy)benzyloxy)benzyl alcohol in the same manner as described in Example 16.

¹H-NMR (300 MHz, CDCl₃): δ0.88 (9H, t, J=6.9 Hz, OC₁₈H₃₇C18-H), 1.10-1.60 (90H, br, OC₁₈H₃₇C3-17-H), 1.75 (6H, m, OC₁₈H₃₇C2-H), 2.54-2.68 (2H, m, Trt-S—CH₂—), 3.75 (3H, s, -Bzl-OMe), 3.92 (6H, m, OC₁₈H₃₇C1-H), 4.19 (1H, m, fluorene C9-H), 4.26-4.38 (3H, m, fluorene-CH₂—, Cys α-H), 4.88 (2H, s, Ar₁—CH₂—O—Ar₂), 5.16-5.28 (3H, m, NH, CysO—CH₂—Ar₁), 6.42-6.45 (2H, m, Ph C3,5-H), 6.57 (2H, s, Ph C2',6'-H), 7.10-7.45 (20H, m, Ph C6-H, Trt, fluorene C2,3,6,7-H), 7.57 (1H, d, J=7.2 Hz, fluorene C1,8-H), 7.75 (2H, d, J=7.2 Hz, fluorene C4,5-H)

Example 20

Condensation of 2-docosyloxy-4-methoxybenzyl alcohol with Fmoc-Met-OH

2-Docosyloxy-4-methoxybenzyl alcohol (213 mg, 0.46 mmol) was dissolved in chloroform (3 ml), and Fmoc-Met-OH (188 mg, 0.51 mmol) and DMAP (6 mg, 0.05 mmol) were added. EDC HCl (107 mg, 0.56 mmol) was added under ice-cooling, and the mixture was stirred at room temperature for 1 hr. After completion of the reaction, the solvent was evaporated, and the residue was precipitated with acetonitrile (10 ml) to give a condensed product (349 mg, 0.43 mmol, yield 93%).

¹H-NMR (300 MHz, CDCl₃): δ0.88 (3H, t, J=6.8 Hz), 1.21-1.79 (40H, m), 1.96-2.16 (5H, m), 2.43-2.48 (2H, m), 3.78 (3H, s), 3.93 (2H, t, J=6.3 Hz), 4.21 (1H, t, J=3.7 Hz), 4.38-4.51 (3H, m), 5.12-5.24 (2H, m), 6.41-6.43 (2H, m), 7.21 (1H, d, J=8.8 Hz), 7.28-7.42 (4H, m), 7.59 (2H, d, J=7.3 Hz), 7.76 (2H, d, J=7.3 Hz)

Example 21

Condensation of 4-methoxy-2-[3',4',5'-tris(octadecyloxy)cyclohexylmethyloxy]benzyl alcohol with Fmoc-Met-OH The title compound was synthesized from 4-methoxy-2-[3',4',5'-tris(octadecyloxy)cyclohexylmethyloxy]benzyl alcohol in the same manner as described in Example 20.

¹H-NMR (300 MHz, CDCl₃): δ0.88 (9H, t, J=6.8 Hz), 1.21-1.81 (96H, m), 1.95-2.16 (5H, m), 2.45-2.46 (2H, m), 3.64-3.68 (2H, m), 3.77 (2H, t, J=6.3 Hz), 4.17 (1H, t, J=3.7 Hz), 4.37-4.48 (3H, m), 5.12-5.23 (2H, m), 6.39-6.42 (2H, m), 7.23 (1H, d, J=8.8 Hz), 7.29-7.42 (4H, m), 7.59 (2H, d, J=7.3 Hz), 7.75 (2H, d, J=7.3 Hz)

Example 22

Condensation of 2-docosyloxy-4-methoxybenzyl alcohol with Fmoc-Trp(Boc)-OH

2-Docosyloxy-4-methoxybenzyl alcohol (200 mg, 0.43 mmol) was dissolved in chloroform (3 ml), and Fmoc-Trp(Boc)-OH (250 mg, 0.47 mmol) and DMAP (6 mg, 0.05 mmol) were added. EDC.HCl (108 mg, 0.56 mmol) was added under ice-cooling, and the mixture was stirred at room temperature for 2.5 hr. After completion of the reaction, the solvent was evaporated, and the residue was precipitated with acetonitrile (10 ml) to give a condensed product (355 mg, 0.37 mmol, yield 85%).

¹H-NMR (300 MHz, CDCl₃): δ0.86 (3H, t, J=6.8 Hz), 1.22-1.77 (49H, m), 3.21-3.28 (2H, m), 3.79 (3H, s), 3.91 (2H, t, J=6.3 Hz), 4.18 (1H, t, J=3.7 Hz), 4.28-4.37 (3H, m), 4.76-4.79 (1H, m), 5.07-5.21 (2H, m), 6.38-6.41 (2H, m), 7.20 (1H, d, J=8.8 Hz), 7.27-7.55 (11H, m), 7.75 (2H, d, J=7.3 Hz), 8.10 (1H, m)

Example 23

Condensation of 4-methoxy-2-[3',4',5'-tris(octadecyloxy)cyclohexylmethyloxy]benzyl alcohol with Fmoc-Trp(Boc)-OH The title compound was synthesized from 4-methoxy-2-[3',4',5'-tris(octadecyloxy)cyclohexylmethyloxy]benzyl alcohol in the same manner as described in Example 22.

$^1$H-NMR (300 MHz, CDCl$_3$): δ0.88 (9H, t, J=6.8 Hz), 1.20-1.76 (105H, m), 3.24-3.28 (2H, m), 3.63-3.67 (6H, m), 3.78 (3H, s), 4.16 (1H, t, J=3.7 Hz), 4.32-4.35 (3H, m), 4.74-4.76 (1H, m), 5.09-5.20 (2H, m), 6.37-6.39 (2H, m), 7.18 (1H, d, J=8.8 Hz), 7.26-7.52 (11H, m), 7.74 (2H, d, J=7.3 Hz), 8.09 (1H, m)

Comparative Example 1

Condensation of 3,4,5-tris(actadecyloxy)benzyl alcohol with Fmoc-Cys(Trt)-OH

The title compound was synthesized from 3,4,5-tris(octadecyloxy)benzyl alcohol in the same manner as described in Example 16.

$^1$H-NMR (300 MHz, CDCl$_3$): δ0.88 (9H, t, J=6.9 Hz, —C$_{17}$H$_{34}$-Me), 1.00-1.60 (90H, alkyl-H), 1.65-1.80 (6H, br, —O—CH$_2$—CH$_2$—C$_{16}$H$_{33}$), 2.50-2.75 (2H, br, Trt-S—CH$_2$—), 3.90 (6H, br, s, —O—CH$_2$—C$_{17}$H$_{35}$), 4.21 (1H, t, J=6.2 Hz, fluorene C9-H), 4.25-4.45 (3H, br, fluorene-CH$_2$—, Cys α-H), 5.04 (2H, s, benzyl-H), 5.26 (1H, d, J=8.4 Hz, N—H), 6.50 (2H, s, Ph C2,6-H), 7.10-7.45 (13H, m, Trt, fluorene C3,4,5,6-H), 7.59 (2H, d, J=6.8 Hz, fluorene C1,8-H), 7.76 (2H, d, J=6.9 Hz, fluorene C4,5-H)

Comparative Example 2

Condensation of 2,4-di(docosyloxy)benzyl alcohol with Fmoc-Cys(Trt)-OH

The title compound was synthesized from 2,4-di(docosyloxy)benzyl alcohol in the same manner as described in Example 16.

$^1$H-NMR (300 MHz, CDCl$_3$): δ0.88 (6H, t, J=6.9 Hz, OC$_{22}$H$_{45}$C22-H), 1.10-1.60 (76H, br, OC$_{22}$H$_{45}$C3-21-H), 1.73 (4H, m, OC$_{22}$H$_{45}$C2-H) 2.63 (2H, m, Trt-S—CH$_2$—), 3.88 (4H, m, OC$_{22}$H$_{45}$C1-H), 4.22 (1H, t, J=6.8 Hz, fluorene C9-H), 4.27-4.35 (3H, m, fluorene-CH$_2$—, Cys α-H), 5.15 (2H, s, CysO—CH$_2$—Ar$_1$), 5.27 (1H, d, J=8.0 Hz, NH), 6.37-6.39 (2H, m, Ph C3,5-H), 7.10-7.41 (20H, m, Ph C6-H, Trt, fluorene C2,3,6,7-H), 7.59 (2H, d, J=7.2 Hz, fluorene C1,8-H), 7.75 (2H, d, J=7.2 Hz, fluorene C4,5-H)

Comparative Example 3

Condensation of 3,4,5-tris(octadecyloxy)benzyl alcohol with Fmoc-Met-OH

The title compound was synthesized from 3,4,5-tris(octadecyloxy)benzyl alcohol in the same manner as described in Example 20.

$^1$H-NMR (300 MHz, CDCl$_3$): δ0.87 (9H, t, J=6.8 Hz), 1.44-1.79 (105H, m), 3.20-3.28 (2H, m), 3.89-3.91 (6H, m), 4.21 (1H, m), 4.36 (2H, d, J=6.0 Hz), 4.78-5.09 (3H, m), 6.46 (2H, d, J=6.0 Hz), 7.18-7.55 (11H, m), 7.75 (2H, d, J=6.0 Hz), 8.11 (1H, m)

Comparative Example 4

Condensation of 3,4,5-tris(octadecyloxy)benzyl alcohol and Fmoc-Trp(Boc)-OH

The title compound was synthesized from 3,4,5-tris(octadecyloxy)benzyl alcohol in the same manner as described in Example 22.

$^1$H-NMR (300 MHz, CDCl$_3$): δ0.87 (9H, t, J=6.8 Hz), 1.21-1.84 (96H, m), 2.00-2.04 (5H, m), 2.48 (2H, m), 3.92-3.96 (6H, m), 4.19-4.24 (1H, m), 4.40 (d, 2H, J=6.0 Hz), 4.53-4.55 (1H, m), 5.08 (2H, m), 6.52 (s, 2H), 7.27 (2H, d, J=6.0 Hz), 7.38 (2H, d, J=6.0 Hz), 7.58 (2H, d, J=6.0 Hz), 7.76 (2H, d, J=6.0 Hz)

Example 24

Introduction of Fmoc-Leu-OH into benzyl alcohol compound (anchor)

4-(12'-Docosyloxy-1'-dodecyloxy)-2-methoxybenzyl alcohol (hereinafter to be sometimes referred to as Bzl (2-MeO-4-OC$_{12}$OC$_{22}$)—OH, 651 mg, 1.01 mmol) was dissolved in chloroform (7 mL), Fmoc-Leu-OH (711 mg, 2.01 mmol) and dimethylaminopyridine (24.6 mg, 201 μmol) were added at room temperature, and EDC HCl (424 mg, 2.21 mmol) was added in an ice bath. The mixture was warmed to room temperature, and stirred overnight. The reaction mixture was concentrated under reduced pressure, methanol was added to the residue, and the precipitated crystals were collected by filtration to give Fmoc-Leu-OBzl (2-MeO-4-OC$_{12}$OC$_{22}$) (942 mg, 95% yield relative to Bzl (2-MeO-4-OC$_{12}$OC$_{22}$)—OH).

$^1$H-NMR (300 MHz, CDCl$_3$): δ0.80-1.00 (9H, m, —CO$_{21}$H$_{42}$-Me, LeuMe), 1.15-1.85 (61H, br, Alkyl-H, Leu-CH$_2$—CHMe$_2$), 3.39 (4H, t, J=6.7 Hz, —C$_{11}$H$_{22}$—CH$_2$—O—CH$_2$—C$_{21}$H$_{43}$), 3.78 (3H, s, OMe), 3.92 (2H, t, J=6.5 Hz, Ar—O—CH$_2$—), 4.15-4.25 (1H, m, fluorene C9-H), 4.30-4.50 (3H, m, fluorene-CH$_2$—O—, Leu α-H), 5.05-5.25 (3H, m, benzyl-H, Fmoc-NH—), 6.35-6.45 (2H, m, Ph C3,5-H), 7.19 (1H, d, J=8.7 Hz, Ph C6-H), 7.31 (2H, d, J=7.4 Hz, fluorene C2,7-H), 7.40 (2H, t, J=7.3 Hz, fluorene C3,6-H), 7.59 (2H, d, J=7.3 Hz, fluorene C1,8-H), 7.76 (2H, d, J=7.4 Hz, fluorene C4,5-H)

Example 25

Removal of Fmoc group from Fmoc-Leu-OBzl (2-MeO-4-OC$_{12}$OC$_{22}$), followed by condensation with Fmoc-Leu-OH (i) The crude crystals (942 mg) of Fmoc-Leu-OBzl (2-MeO-4-OC$_{12}$OC$_{22}$) were dissolved in chloroform (9 mL), and diethylamine (1.99 mL, 19.2 mmol) was added dropwise under ice-cooling. The mixture was warmed to room temperature, acetonitrile (4.5 mL) was added, and the mixture was stirred for 3.5 hr. The reaction mixture was concentrated under reduced pressure, and the residue was precipitated with acetonitrile (10 mL) to give Leu-OBzl (2-MeO-4-OC$_{12}$OC$_{22}$) as wet crystals.

$^1$H-NMR (300 MHz, CDCl$_3$): δ0.80-1.00 (9H, m, —CO$_{21}$H$_{42}$-Me, Leu Me), 1.15-1.85 (61H, br, Alkyl-H, Leu-CH$_2$—CHMe$_2$), 3.39 (4H, t, J=6.7 Hz, —C$_{11}$H$_{22}$—CH$_2$—O—CH$_2$—C$_{21}$H$_{43}$), 3.46 (1H, dd, J=5.9, 8.4 Hz, Leu α-H), 3.81 (3H, s, OMe), 3.95 (2H, t, J=6.5 Hz, Ar—O—CH$_2$—), 5.11 (2H, s, benzyl-H), 6.40-6.50 (2H, m, Ph C3,5-H), 7.20 (1H, d, J=8.6 Hz, Ph C6-H)

(ii) The obtained wet crystals of Leu-OBzl (2-MeO-4-OC$_{12}$OC$_{22}$) were dissolved in chloroform (13 mL), Fmoc-Leu-OH (373 mg, 1.06 mmol) and HOBt (14.3 mg, 106 μmol) were added at room temperature, and EDC.HCl (223 mg, 1.16 mmol) was further added under ice-cooling. The mixture was warmed to room temperature, stirred overnight, and concentrated under reduced pressure. Methanol (10 mL) was added to the residue, and the precipitate was collected by filtration to give Fmoc-Leu-Leu-OBzl (2-MeO-4-OC$_{12}$OC$_{22}$) (1.02 g, 93% yield relative to Bzl (2-MeO-4-OC$_{12}$OC$_{22}$)OH).

$^1$H-NMR (300 MHz, CDCl$_3$): δ0.80-1.00 (15H, m, —OC$_{21}$H$_{42}$-Me, Leu Me), 1.15-1.85 (64H, br, Alkyl-H, Leu —CH$_2$—CHMe$_2$), 3.39 (4H, t, J=6.7 Hz, —C$_{11}$H$_{22}$—CH$_2$—O—CH$_2$—H$_{21}$H$_{43}$), 3.79 (3H, s, OMe), 3.94 (2H, t, J=6.3 Hz, Ar—O—CH$_2$—), 4.10-4.30 (2H, m, fluorene C9-H, Leu α-H), 4.39 (2H, d, J=7.1 Hz, fluorene-CH$_2$—O—), 4.55-4.70 (1H, br, Leu α-H), 5.00-5.30 (3H, m, benzyl-H, —NH—), 6.20-6.30 (1H, br, —NH—), 6.40-6.50 (2H, m, Ph C3,5-H), 7.17 (1H, d, J=7.9 Hz, Ph C6-H), 7.32 (2H, d, J=7.4 Hz, fluorene C2,7-H), 7.40 (2H, t, J=7.4 Hz, fluorene C3,6-H), 7.58 (2H, d, J=7.2 Hz, fluorene C1,8-H), 7.76 (2H, d, J=7.4 Hz, fluorene C4,5-H)

Example 26

Removal of Fmoc group from Fmoc-Leu-Leu-OBzl (2-MeO-4-OC$_{12}$OC$_{22}$), followed by condensation with Fmoc-D-Lys(Boc)-OH (i) Fmoc-Leu-Leu-OBzl (2-MeO-4-OC$_{12}$OC$_{22}$) (1.02 g) was dissolved in chloroform (10 mL), and diethylamine (1.94 mL, 18.7 mmol) was added dropwise under ice-cooling. The mixture was warmed to room temperature, acetonitrile (5 mL) was added, and the mixture was stirred for 2.5 hr. Diethylamine (970 µL, 9.35 mmol) was added, and the mixture was further stirred for 1 hr. The reaction mixture was concentrated under reduced pressure, and the residue was precipitated with acetonitrile (10 mL) to give Leu-Leu-OBzl (2-MeO-4-OC$_{12}$OC$_{22}$) as wet crystals.

$^1$H-NMR (300 MHz, CDCl$_3$): δ0.80-1.00 (15H, m, —OC$_{21}$H$_{42}$-Me, Leu Me), 1.15-1.85 (70H, br, Alkyl-H, Leu-CH$_2$—CHMe$_2$), 3.39 (4H, t, J=6.7 Hz, —C$_{11}$H$_{22}$—CH$_2$—O—CH$_2$—C$_{21}$H$_{43}$), 3.46 (1H, dd, J=5.9, 8.4 Hz, Leu α-H), 3.81 (3H, s, OMe), 3.95 (2H, t, J=6.5 Hz, Ar—O—CH$_2$—), 5.11 (2H, s, benzyl-H), 6.40-6.50 (2H, m, Ph C3,5-H), 7.20 (1H, d, J=8.6 Hz, Ph C6-H), 7.59 (1H, d, J=8.5 Hz, N—H)

(ii) The obtained wet crystals of Leu-Leu-OBzl (2-MeO-4-OC$_{12}$OC$_{22}$) were dissolved in chloroform (13 mL), Fmoc-D-Lys(Boc)-OH (481 mg, 1.03 mmol) and HOBt (13.9 mg, 103 µmol) were added at room temperature, and EDC HCl (216 mg, 1.13 mmol) was further added under ice-cooling. The mixture was warmed to room temperature, stirred overnight and concentrated under reduced pressure. The residue was precipitated with methanol (10 mL) to give Fmoc-D-Lys(Boc)-Leu-Leu-OBzl (2-MeO-4-OC$_{12}$OC$_{22}$) (1.14 g, 86% yield relative to Bzl (2-MeO-4-OC$_{12}$OC$_{22}$)OH).

$^1$H-NMR (300 MHz, CDCl$_3$): δ0.80-1.00 (15H, m, —OC$_{21}$H$_{42}$-Me, Leu Me), 1.15-1.85 (79H, br, Alkyl-H, Leu —CH$_2$—CHMe$_2$, Lys Boc-NH—CH$_2$—(CH$_2$)$_3$—), 3.05-3.20 (2H, br, Boc-NH—CH$_2$—), 3.39 (4H, t, J=6.7 Hz, —C$_{11}$H$_{22}$CH$_2$—O—CH$_2$—C$_{21}$H$_{43}$), 3.77 (3H, s, OMe), 3.93 (2H, t, J=6.5 Hz, Ar—O—CH$_2$—), 4.05-4.15 (1H, br, —NH—CHR—CO—), 4.15-4.25 (1H, m, fluorene C9-H), 4.35-4.50 (3H, br, fluorene-CH$_2$—, —NH—CHR—CO— or —NH—), 4.50-4.70 (2H, br, —NH—CHR—CO— or —NH—), 5.09 (2H, q, J=12.0 Hz, benzyl-H), 5.45-5.55 (1H, br, —NH—), 6.35-6.55 (4H, m, Ph C3,5-H, —NH—), 7.16 (1H, d, J=7.9 Hz, Ph C6-H), 7.32 (2H, d, J=7.3 Hz, fluorene C2,7-H), 7.40 (2H, t, J=7.3 Hz, fluorene C3,6-H), 7.59 (2H, d, J=7.1 Hz, fluorene C1,8-H), 7.76 (2H, d, J=7.4 Hz, fluorene C4,5-H)

Example 27

Removal of Fmoc group from Fmoc-D-Lys(Boc)-Leu-Leu-OBzl (2-MeO-4-OC$_{12}$OC$_{22}$), followed by condensation with Fmoc-D-Lys(Boc)-OH (i) Fmoc-D-Lys(Boc)-Leu-Leu-OBzl(2-MeO-4-OC$_{12}$OC$_{22}$) (1.14 g) was dissolved in chloroform (12 mL), and diethylamine (2.68 mL, 25.8 mmol) was added dropwise under ice-cooling. The mixture was warmed to room temperature, acetonitrile (4 mL) was added, and the mixture was stirred for 2 hr. Diethylamine (890 µL, 8.58 mmol) was added, and the mixture was further stirred for 0.5 hr. The reaction mixture was concentrated under reduced pressure, and the residue was precipitated with acetonitrile (10 mL) to give D-Lys(Boc)-Leu-Leu-OBzl (2-MeO-4-OC$_{12}$OC$_{22}$) as wet crystals.

$^1$H-NMR (300 MHz, CDCl$_3$): δ0.80-1.00 (15H, m, —OC$_{21}$H$_{42}$-Me, Leu Me), 1.15-1.85 (79H, br, Alkyl-H, Leu —CH$_2$—CHMe$_2$, Lys Boc-NH—CH$_2$—(CH$_2$)$_3$), 3.11 (2H, br, d, J=5.6 Hz, Boc-NH—CH$_2$—), 3.39 (5H, t, J=6.7 Hz, —C$_{11}$H$_{22}$—CH$_2$—O—CH$_2$—C$_{21}$H$_{43}$, —NH—CHR—CO—), 3.80 (3H, s, OMe), 3.95 (3H, t, J=6.5 Hz, Ar—O—CH$_2$—, —NH—CHR—CO—), 4.30-4.45 (1H, br, —NH—CHR—CO—), 4.50-4.70 (2H, br, —NH$_2$—), 5.08 (1H, d, J=11.9 Hz, benzyl-H), 5.15 (1H, d, J=11.9 Hz, benzyl-H), 6.35-6.50 (3H, m, Ph C3,5-H, N—H), 6.57 (1H, d, J=8.1 Hz, N—H), 7.18 (1H, d, J=8.9 Hz, Ph C6-H), 7.64 (1H, d, J=8.0 Hz)

(ii) The obtained wet crystals of D-Lys(Boc)-Leu-Leu-OBzl (2-MeO-4-OC$_{12}$OC$_{22}$) were dissolved in chloroform (15 mL), Fmoc-D-Lys(Boc)-OH (444 mg, 948 µmol) and HOBt (12.8 mg, 94.7 µmol) were added at room temperature, and EDC HCl (200 mg, 1.04 mmol) was further added under ice-cooling. The mixture was warmed to room temperature and stirred overnight. Chloroform (20 mL), Fmoc-D-Lys(Boc)-OH (89 mg, 190 µmol) and EDC.HCl (40 mg, 210 µmol) were added, and the mixture was further stirred for 1 hr and concentrated under reduced pressure. The residue was precipitated with methanol (15 mL) to give Fmoc-D-Lys(Boc)-D-Lys(Boc)-Leu-Leu-OBzl (2-MeO-4-OC$_{12}$OC$_{22}$) (1.35 g, 85% yield relative to Bzl (2-MeO-4-OC$_{12}$OC$_{22}$)OH).

$^1$H-NMR (300 MHz, CDCl$_3$): δ0.80-1.00 (15H, m, —OC$_{21}$H$_{42}$-Me, Leu Me), 1.15-2.00 (94H, br, Alkyl-H, -Leu —CH$_2$—CHMe$_2$, Lys Boc-NH—CH$_2$—(CH$_2$)$_3$), 3.00-3.20 (4H, br, Boc-NH—CH$_2$—), 3.10-3.30 (1H, m, —NH—CHR—CO—), 3.39 (4H, t, J=6.7 Hz, —C$_{11}$H$_{22}$—CH$_2$—O—CH$_2$—C$_{21}$H$_{43}$), 3.77 (3H, s, OMe), 3.93 (2H, t, J=6.5 Hz, Ar—O—CH$_2$—), 4.05-4.20 (1H, br, —NH—CHR—CO—), 4.15-4.25 (1H, m, fluorene C9-H), 4.30-4.50 (3H, br, fluorene-CH$_2$—, —NH—CHR—CO— or —NH—), 4.50-4.75 (2H, br, —NH—CHR—CO— or —NH—), 5.04 (1H, d, J=11.9 Hz, benzyl-H), 5.14 (1H, d, J=11.9 Hz, benzyl-H), 5.60-5.80 (1H, br, —NH—), 6.40-6.60 (3H, m, Ph C3,5-H, —NH—), 6.70-6.80 (1H, br, —NH—), 7.16 (1H, d, J=8.2 Hz, Ph C6-H), 7.32 (2H, d, J=7.2 Hz, fluorene C2,7-H), 7.39 (2H, t, J=7.2 Hz, fluorene C3,6-H), 7.61 (2H, t, J=5.6 Hz, fluorene C1,8-H), 7.76 (2H, d, fluorene C4,5-H)

Example 28

Removal of anchor from Fmoc-D-Lys(Boc)-D-Lys(Boc)-Leu-Leu-OBzl (2-MeO-4-OC$_{12}$OC$_{22}$)

The crude crystals (1.23 g) of Fmoc-D-Lys(Boc)-D-Lys(Boc)-Leu-Leu-OBzl (2-MeO-4-OC$_{12}$OC$_{22}$) were dissolved in a mixture of chloroform (12 mL) and heptane (12 mL), and 3% trifluoroacetic acid/(chloroform-heptane=1:1) solution was added dropwise under ice-cooling. The reaction mixture was stirred in a water bath at 10-15° C. for 3 hr, and 2.5% aqueous sodium hydrogen carbonate solution (18 mL) and chloroform (18 mL) were added. 0.1N Hydrochloric acid was added, and the aqueous layer was adjusted to pH 2. The aqueous layer was removed, and the organic layer was washed 3 times with purified water (10 mL). The combined organic layers were concentrated under reduced pressure, and heptane (30 mL) was added to the residue. The precipitated crystals were washed at 40° C. and collected by filtration to give Fmoc-D-Lys(Boc)-D-Lys(Boc)-Leu-Leu-OH (800 mg, 93%).

MS (MH$^-$) 921.5

Example 29

Removal of anchor (concomitant with removal of Boc group) from Fmoc-D-Lys(Boc)-D-Lys(Boc)-Leu-Leu-OBzl (2-MeO-4-OC$_{12}$OC$_{22}$)

The crude crystals (100 mg) of Fmoc-D-Lys(Boc)-D-Lys (Boc)-Leu-Leu-OBzl (2-MeO-4-OC$_{12}$OC$_{22}$) were added to a solution (2 ml) of trifluoroacetic acid:triisopropylsilane:water=95:2.5:2.5 under ice-cooling, and the mixture was stirred at room temperature for 2 hr. The reaction mixture was concentrated under reduced pressure, and methyl tert-butyl ether (MTBE)/cyclohexane was added to the residue. The precipitate was washed at 40° C. and collected by filtration to give Fmoc-D-Lys-D-Lys-Leu-Leu-OH (29 mg).

MS (MH$^+$) 723.3

Experimental Example 1

Comparison of Anchor of the Present Invention and Known Anchor in Yield of Deprotection Reaction of Anchor-Protected Form of Fmoc-Cys(Trt)-OH

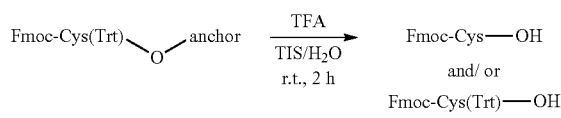

Test Compounds

The compounds described in the aforementioned Examples 16, 17, 18 and 19, wherein Fmoc-Cys(Trt)-OH was introduced into the four kinds of anchors of the present invention, (hereinafter to be referred to as Example compounds 16, 17, 18 and 19) were used as test compounds.

In addition, Fmoc-Cys(Trt)-OBzl (3,4,5-tri-OC$_{18}$) obtained by introducing Fmoc-Cys(Trt)-OH into the following formula:

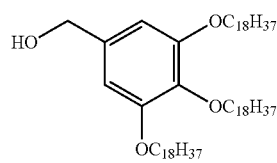

which is the anchor molecule described in the aforementioned non-patent document 1 and patent document 1 (hereinafter to be referred to as Bzl(3,4,5-tri-OC$_{18}$)OH, and Fmoc-Cys(Trt)-OBzl (2,4-di-OC$_{22}$) obtained by introducing Fmoc-Cys(Trt)-OH into the following formula:

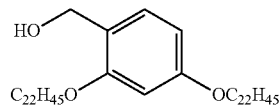

which is the anchor molecule described in the aforementioned patent document 3 (hereinafter to be referred to as Bzl(2,4-di-OC$_{22}$)OH), that is, the compounds described in the aforementioned Comparative Examples 1 and 2, respectively, were used as test compounds (hereinafter to be referred to as Comparative Example compounds 1 and 2).

Experiment Method (i) To each test compound was added trifluoroacetic acid (TFA:H$_2$O:TIS=95:2.5:2.5) in triisopropylsilane-water at room temperature, and the mixture was stirred for 2 hr. The total yield of the anchor-deprotected forms, that is, Fmoc-Cys-OH and Fmoc-Cys(Trt)-OH, was measured and the yield was calculated (Table 1).

(ii) Each test compound was added to 2% trifluoroacetic acid-chloroform solution at room temperature, and the mixture was stirred for 1 hr. The total yield of the anchor-deprotected forms, that is, Fmoc-Cys-OH and Fmoc-Cys(Trt)-OH, was measured, and the yield was calculated (Table 2).

Experiment Results

In both cases of the above-mentioned (i) and (ii), the starting material disappeared, and the deprotection reaction of Example compounds 16-19 produced only the anchor-deprotected forms in high yield. However, in the reactions of Comparative Example compounds 1 and 2, wherein 2 or 3 hydroxyl groups substituted by long chain aliphatic hydrocarbon groups were introduced into the anchor group, the yield of the deprotected forms decreased (see Table 1 and Table 2). Therefrom it has been confirmed that the anchor compound of the present invention having only one hydroxyl group substituted by a long chain aliphatic hydrocarbon group is a protecting reagent with broad utility, which permits efficient progress of the removal reaction of the anchor in a high yield even when the reaction substrate contains a reactive functional group such as a thiol group and the like.

TABLE 1

| test compound | yield(%) |
|---|---|
| Example compound 16 | 94 |
| Example compound 17 | 97 |
| Example compound 18 | 100 |
| Comparative Example compound 1 | 23 |
| Comparative Example compound 2 | 68 |

TABLE 2

| test compound | yield(%) |
|---|---|
| Example compound 16 | 100 |
| Example compound 17 | 98 |
| Example compound 19 | 97 |
| Comparative Example compound 2 | 84 |

Experimental Example 2

Comparison of Anchor of the Present Invention and Known Anchor in Yield of Deprotection Reaction of Anchor-Protected Form of Fmoc-Trp(Boc)-OH and Anchor-Protected form of Fmoc-Met-OH Test Compounds The compounds described in the aforementioned Examples 20 and 21, and Examples 22 and 23, wherein Fmoc-Met-OH and Fmoc-Trp(Boc)-OH were introduced into the two kinds of anchors of the present invention, (hereinafter to be referred to as is Example compounds 20, 21, 22 and 23) were used as test compounds.

In addition, Fmoc-Met-OBzl (3,4,5-tri-$OC_{18}$) and Fmoc-Trp(Boc)-OBzl (3,4,5-tri-$OC_{18}$) obtained by introducing Fmoc-Met-OH and Fmoc-Trp(Boc)-OH, respectively, into the following formula:

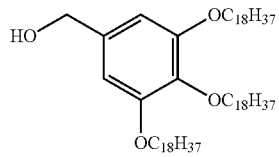

which is the anchor molecule described in the aforementioned non-patent document 1 (hereinafter to be referred to as Bzl (3,4,5-tri-$OC_{18}$)OH), that is, the compounds described in the aforementioned Comparative Examples 3 and 4 were used as test compounds (hereinafter to be referred to as Comparative Example compounds 3 and 4).

Experiment Method (iii) To each test compound was added trifluoroacetic acid (TFA:$H_2O$:TIS=95:2.5:2.5) in triisopropylsilane-water at room temperature, and the mixture was stirred for 4 hr. The yield of the anchor-deprotected form, i.e., Fmoc-Met-OH, and that of the alkylated form (the compound of the following formula A) were measured and the yields were calculated (Table 3).

(iv) To each test compound was added trifluoroacetic acid (TFA:$H_2O$:TIS=95:2.5:2.5) in triisopropylsilane-water at room temperature, and the mixture was stirred for 4 hr. The yield of the anchor-deprotected form, i.e., Fmoc-Trp-OH, and that of the alkylated form (the compound of the following formula B) were measured, and the yields were calculated (Table 4).

Experimental Results

In both cases of the above-mentioned (iii) and (iv), the starting material disappeared, and the deprotection reaction of Example compounds 20-23 produced only the anchor-deprotected form (Fmoc-Met-OH or Fmoc-Trp-OH) in high yield. However, in the reactions of Comparative Example compounds 3 and 4, into which an anchor group wherein 3 hydroxyl groups were substituted by long chain aliphatic hydrocarbon groups was introduced, the yield of the anchor-deprotected form remarkably decreased (see Table 3 and Table 4), and alkylated forms (A, B) wherein a 3,4,5-tris(octadecyloxy)benzyl group derived from the anchor group was introduced into the methylthio group of Fmoc-Met-OH and the indolyl group of Fmoc-Trp-OH, respectively, were by-produced in large amounts.

The chemical structure of each of the above-mentioned alkylated forms was confirmed by $^1$H-NMR.

$^1$H-NMR (300 MHz, $CDCl_3$) for A: δ0.87 (9H, t, J=6.9 Hz), 1.39-1.87 (96H, m), 2.01-2.25 (7H, m), 3.42-4.52 (2H, m), 3.88-3.96 (6H, m), 4.21-4.26 (1H, m), 4.34-4.36 (1H, m), 4.42-4.51 (2H, m), 6.53 (2H, dd, J=11.2 Hz, 3.1 Hz), 7.27-7.43 (4H, m), 7.60 (2H, m), 7.78 (2H, m);

$^1$H-NMR (300 MHz, $CDCl_3$) for B: δ0.86 (9H, t, J=6.8 Hz), 1.20-1.77 (96H, m), 3.29 (2H, m), 3.79-3.90 (8H, m), 4.20-4.23 (1H, m), 4.27-4.51 (3H, m), 6.48 (2H, m), 7.31-7.75 (12H, m)

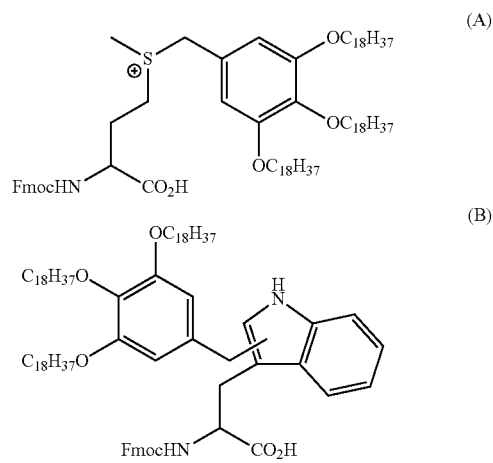

Therefrom it has been confirmed that the anchor compound of the present invention having only one hydroxyl group substituted by a long chain aliphatic hydrocarbon group can suppress side reactions such as alkylation (benzylation) derived from an anchor group and the like, and is a protecting reagent with broad utility, which permits efficient progress of the removal reaction of the anchor in a high yield even when the reaction substrate contains a reactive functional group such as a methylthio group, an indolyl group and the like.

TABLE 3

| test compound | yield (%) | alkylated form (%) |
| --- | --- | --- |
| Example compound 20 | 87 | N.D. |
| Example compound 21 | 88 | N.D. |
| Comparative Example compound 3 | 29 | 65 |

N.D.: not detected

TABLE 4

| test compound | yield (%) | alkylated form (%) |
| --- | --- | --- |
| Example compound 22 | 78 | N.D. |
| Example compound 23 | 96 | N.D. |
| Comparative Example compound 4 | 26 | 68 |

N.D.: not detected

As mentioned above, when the aforementioned known protecting reagent (anchor), that is, a benzyl alcohol type anchor having two or three long chain alkoxy groups on the same benzene ring, is used, side reactions such as alkylation of amino acid residue by alkyl cation (benzyl cation) and the like derived from the anchor occur during removal of the anchor under acidic conditions, and the yield of the anchor-deprotected product markedly decreases.

In view of these results, it is considered that the presence of plural long chain alkoxy groups enhances electron-donatability on the benzene ring, which in turn stabilizes benzyl cation species derived from a dissociated anchor during removal of the anchor under acidic conditions, and the cation species promotes alkylation of nucleophilic groups such as a thiol group of a cysteine residue, a methylthio group of a methionine residue, an indolyl group of a tryptophan residue and the like in the reaction substrate. Thus, it has been clarified that peptide synthesis including amino acid residues (e.g., Cys, Trp, His, Met etc.) capable of reacting with benzyl cation derived from the removed anchor is associated with a problem in that a high yield in the final deprotection and the like cannot be ensured when the aforementioned known protecting reagents are used.

INDUSTRIAL APPLICABILITY

Using the particular benzylic compound of the present invention, a useful benzylic compound can be provided, which enables reactions to be performed in a homogeneous liquid phase, can be used as a protecting reagent (anchor) permitting isolation and purification by filtration and washing alone by changing the solvent composition after the reaction, and affords a resulting product in a high yield and at high purity while suppressing an alkylation reaction during deprotection even under acidic conditions. In addition, the present invention also provides a useful peptide synthesis reaction, and further, a useful organic synthesis reaction (including an oligonucleotide synthesis reaction) using the particular benzylic compound of the present invention.

While some of the embodiments of the present invention have been described in detail in the above, it will, however, be evident for those of ordinary skill in the art that various modifications and changes may be made to the particular embodiments shown without substantially departing from the novel teaching and advantages of the present invention. Such modifications and changes are encompassed in the spirit and scope of the present invention as set forth in the appended claims.

What is claimed is:

1. A benzylic compound represented by formula (I):

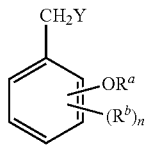

wherein

Y is a hydroxyl group or an —NHR group;

R is a hydrogen atom, an alkyl group or an aralkyl group;

each $R^b$ is independently an alkoxy group having a carbon number of 1 to 6, a halogen atom, or an alkyl group having a carbon number of 1 to 6, which is optionally substituted by one or more halogen atoms;

n is an integer of 0-4; and $R^a$ is represented by formula (b), (c) or (d):

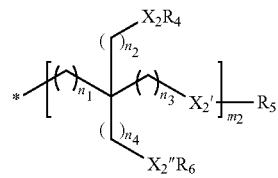

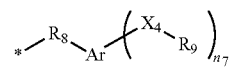

wherein
* indicates the position of a bond;
$m_2$ is 1 or 2;
$n_1$ and $n_3$ are each independently an integer of 0-2;
$n_2$ and $n_4$ are each independently an integer of 0-2, except that $n_2$ and $n_4$ are not both 0;
each $X_2$, $X_2'$ in the number of $m_2$ and $X_2''$ are independently a single bond, —O—, —S—, —COO—, —OCONH—, —NHCO— or —CONH—;
each $R_4$ and each $R_6$ are independently a hydrogen atom, a methyl group or an aliphatic hydrocarbon group having a carbon number of not less than 5;
$R_5$ is an aliphatic hydrocarbon group having a carbon number of not less than 5;
$m_3$ is an integer of 0-15;
$n_5$ is an integer of 0-11;
$n_6$ is an integer of 0-5;
each $X_3$ is independently a single bond, —O—, —S—, —COO—, —OCONH—, —NHCO— or —CONH—;
each $R_7$ is independently a hydrogen atom, a methyl group or an aliphatic hydrocarbon group having a carbon number of not less than 5;
each $X_4$ is independently a single bond, —O—, —S—, —COO—, —OCONH—, —NHCO— or —CONH;
$R_8$ is a divalent aliphatic hydrocarbon group;
each $R_9$ is independently an alkyl group having a carbon number of 14-30;
$n_7$ is an integer of 1-5; and
Ar is an arylene group.

2. The benzylic compound according to claim 1, wherein $R^a$ is represented by formula (b).

3. The benzylic compound according to claim 1, wherein $R^a$ is represented by formula (c).

4. The benzylic compound according to claim 1, wherein $R^a$ is represented by formula (d).

5. The benzylic compound according to claim 1, wherein the total carbon number of the organic group for Ra is 14-200.

6. The benzylic compound according to claim 1, wherein the total carbon number of the organic group for Ra is 30-80.

7. The benzylic compound according to claim 1, wherein n is an integer of 0-2, and each Rb is independently an alkoxy group having a carbon number of 1 to 4.

8. The benzylic compound according to claim 1, wherein ORa is present at the 2-position or the 4-position on the benzene ring.

9. The benzylic compound according to claim 1, wherein Rb is a methoxy group.

10. The benzylic compound according to claim 1, wherein Y is a hydroxyl group.

11. The benzylic compound according to claim 1, wherein Y is an —NHR group wherein R is as defined in claim 1.

12. The benzylic compound according to claim 1, which is selected from the group consisting of 4-methoxy-2-[3',4',5'-tris(octadecyloxy)benzyloxy]benzyl alcohol, 2-[3',5'-di(docosyloxy)benzyloxy]-4-methoxybenzyl alcohol, 2-methoxy-4-[2',2',2'-tris(octadecyloxymethyl)ethoxy]benzyl alcohol, 2-methoxy-4-[2',2',2'-tris(octadecyloxymethyl)ethoxy]benzylamine, 4-methoxy-2-[3',4',5'-tris(octadecyloxy)cyclohexylmethyloxy]benzyl alcohol, and 4-[3',4',5'-tris(octadecyloxy)cyclohexylmethyloxy]benzyl alcohol.

13. The benzylic compound according to claim 1, which is selected from the group consisting of 2-methoxy-4-[3',4',5'-tris(octadecyloxy)cyclohexylmethyloxy]benzyl alcohol, and 3,5-dimethoxy-4-[3',4',5'-tris(octadecyloxy)cyclohexylmethyloxy]benzyl alcohol.

* * * * *